US006764534B2

(12) United States Patent
McCombs et al.

(10) Patent No.: US 6,764,534 B2
(45) Date of Patent: Jul. 20, 2004

(54) PORTABLE OXYGEN CONCENTRATOR

(75) Inventors: Norman R. McCombs, Tonawanda, NY (US); Robert E. Casey, Buffalo, NY (US); Michael A. Chimiak, Williamsville, NY (US); Andrezj Klimaszewski, Jacksonville, FL (US)

(73) Assignee: AirSep Corporation, Buffalo, NY (US)

( * ) Notice: Subject to any disclaimer, the term of this patent is extended or adjusted under 35 U.S.C. 154(b) by 35 days.

(21) Appl. No.: 10/354,275

(22) Filed: Jan. 30, 2003

(65) Prior Publication Data

US 2003/0167924 A1 Sep. 11, 2003

Related U.S. Application Data

(60) Provisional application No. 60/353,563, filed on Jan. 31, 2002.

(51) Int. Cl.[7] ............................................. B01D 53/047
(52) U.S. Cl. .......................... 96/111; 96/117; 96/130; 96/140; 96/142; 96/418; 96/422
(58) Field of Search .................... 95/130; 96/111, 96/113–117, 130, 139–143, 417–419, 422

(56) References Cited

U.S. PATENT DOCUMENTS

| 3,564,816 | A | * | 2/1971 | Batta | 95/100 |
|---|---|---|---|---|---|
| 3,636,679 | A | * | 1/1972 | Batta | 95/100 |
| 3,717,974 | A | * | 2/1973 | Batta | 95/98 |
| 3,880,616 | A | * | 4/1975 | Myers et al. | 95/26 |
| 3,922,149 | A | * | 11/1975 | Ruder et al. | 95/22 |
| 4,378,982 | A | * | 4/1983 | McCombs | 96/117 |
| 4,545,790 | A | | 10/1985 | Miller et al. | 55/161 |
| 4,576,616 | A | * | 3/1986 | Mottram et al. | 95/96 |
| 4,681,099 | A | * | 7/1987 | Sato et al. | 128/204.23 |
| 4,732,587 | A | | 3/1988 | Koch | 55/162 |
| 4,802,899 | A | * | 2/1989 | Vrana et al. | 96/109 |
| 4,822,384 | A | * | 4/1989 | Kato et al. | 96/110 |
| 5,474,595 | A | * | 12/1995 | McCombs | 95/23 |
| 5,531,807 | A | * | 7/1996 | McCombs | 95/26 |
| 5,730,778 | A | * | 3/1998 | Hill et al. | 95/12 |
| 5,746,806 | A | * | 5/1998 | Aylsworth et al. | 95/8 |
| 5,871,564 | A | * | 2/1999 | McCombs | 95/98 |
| 5,893,944 | A | | 4/1999 | Dong | 96/114 |
| 5,906,672 | A | * | 5/1999 | Michaels et al. | 95/12 |
| 5,917,135 | A | * | 6/1999 | Michaels et al. | 95/11 |
| 6,314,957 | B1 | | 11/2001 | Boissin et al. | 128/204.17 |
| 6,346,139 | B1 | * | 2/2002 | Czabala | 95/130 |
| 6,427,690 | B1 | * | 8/2002 | McCombs et al. | 128/204.26 |
| 6,478,850 | B1 | | 11/2002 | Warren | 95/21 |
| 6,520,176 | B1 | | 2/2003 | Dubois et al. | 128/200.24 |
| 6,551,384 | B1 | | 4/2003 | Ackley et al. | 95/96 |
| 6,558,451 | B2 | * | 5/2003 | McCombs et al. | 95/98 |
| 2002/0029691 | A1 | * | 3/2002 | McCombs et al. | 95/96 |

FOREIGN PATENT DOCUMENTS

| FR | 0006697 | 5/2000 | B01D/53/047 |
|---|---|---|---|
| WO | WO 02/11861 A1 | 2/2002 | B01D/53/047 |

* cited by examiner

Primary Examiner—Robert H. Spitzer
(74) Attorney, Agent, or Firm—Ronald S. Kareken, Esq.; Jaeckle Fleischmann & Mugel, LLP

(57) ABSTRACT

A compact and highly portable combination pressure swing adsorption apparatus and product gas conservation device for medical use, to produce efficiently a gas with a high concentration of oxygen and to deliver the oxygen concentrated gas to a user at selectable times and in selectable doses.

16 Claims, 33 Drawing Sheets

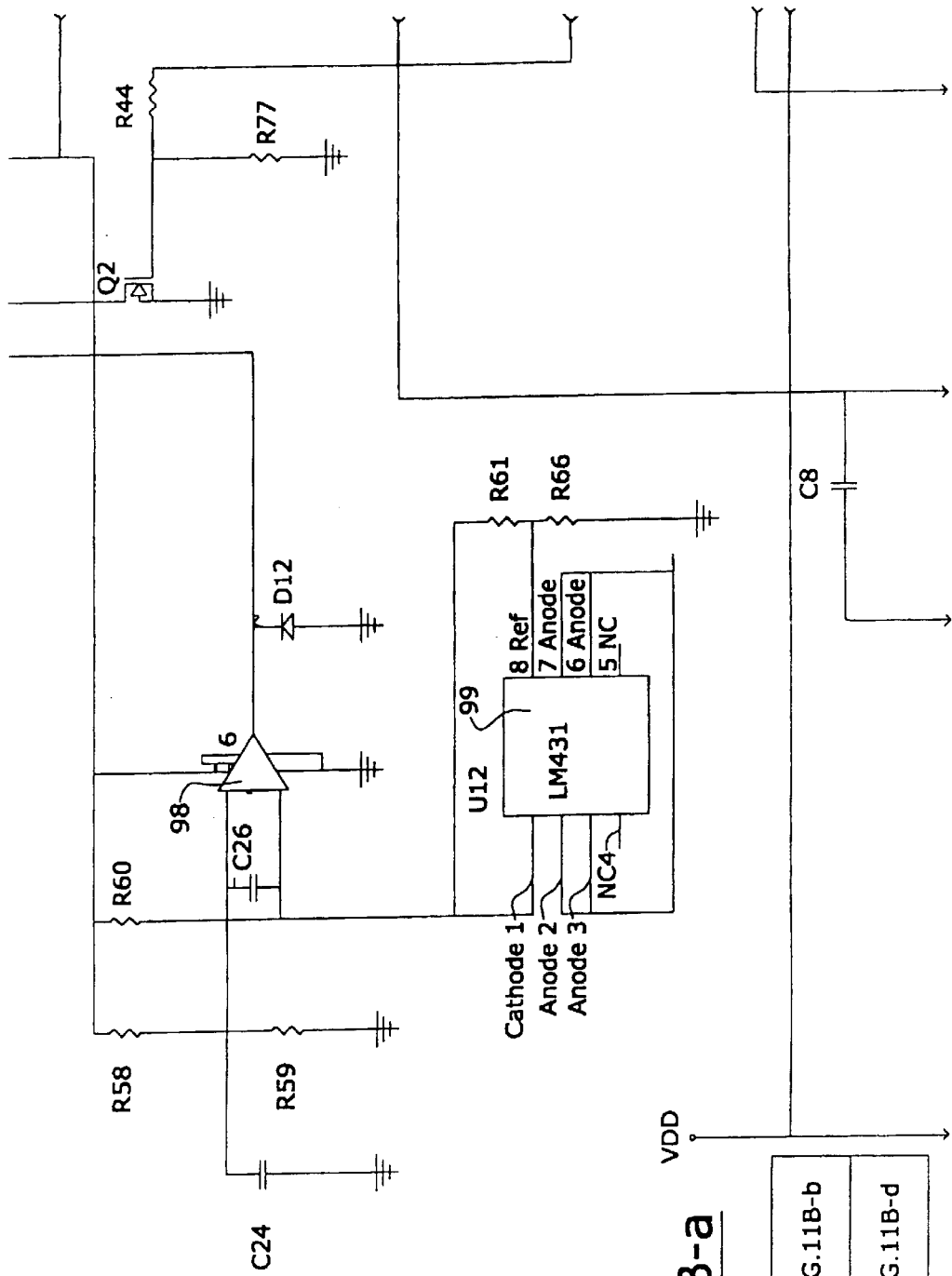
FIG.11B-a

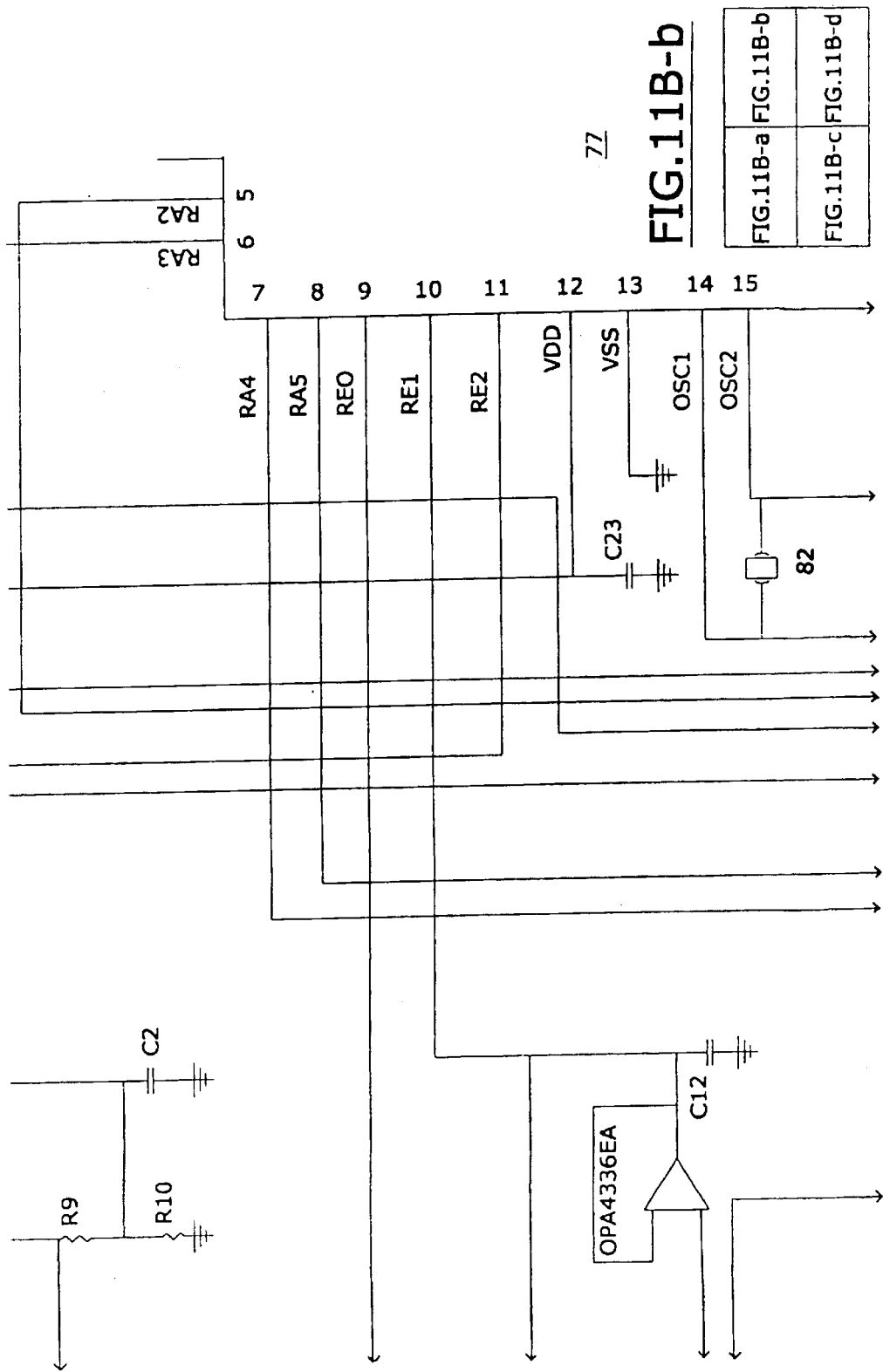

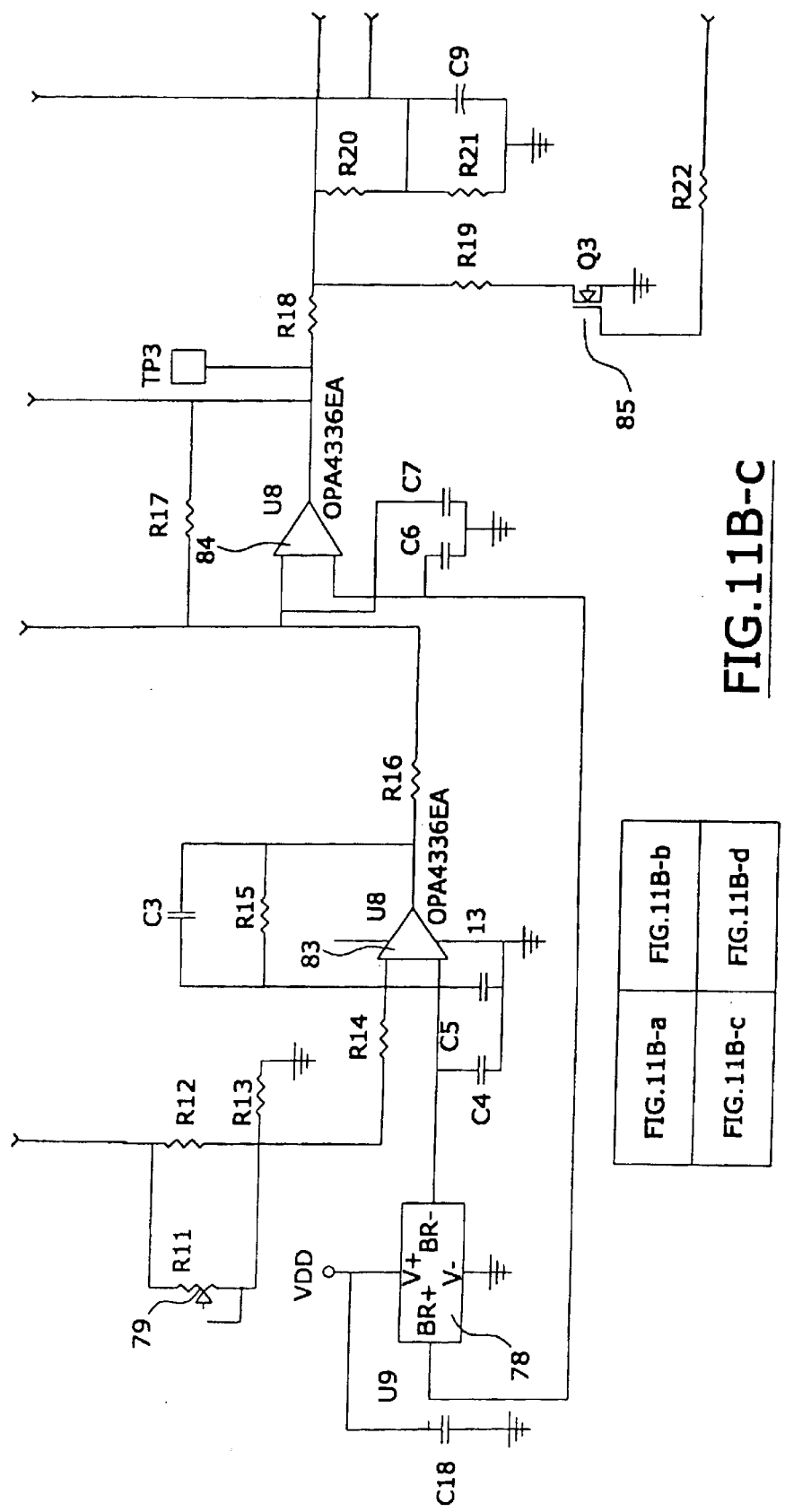
FIG. 11B-c

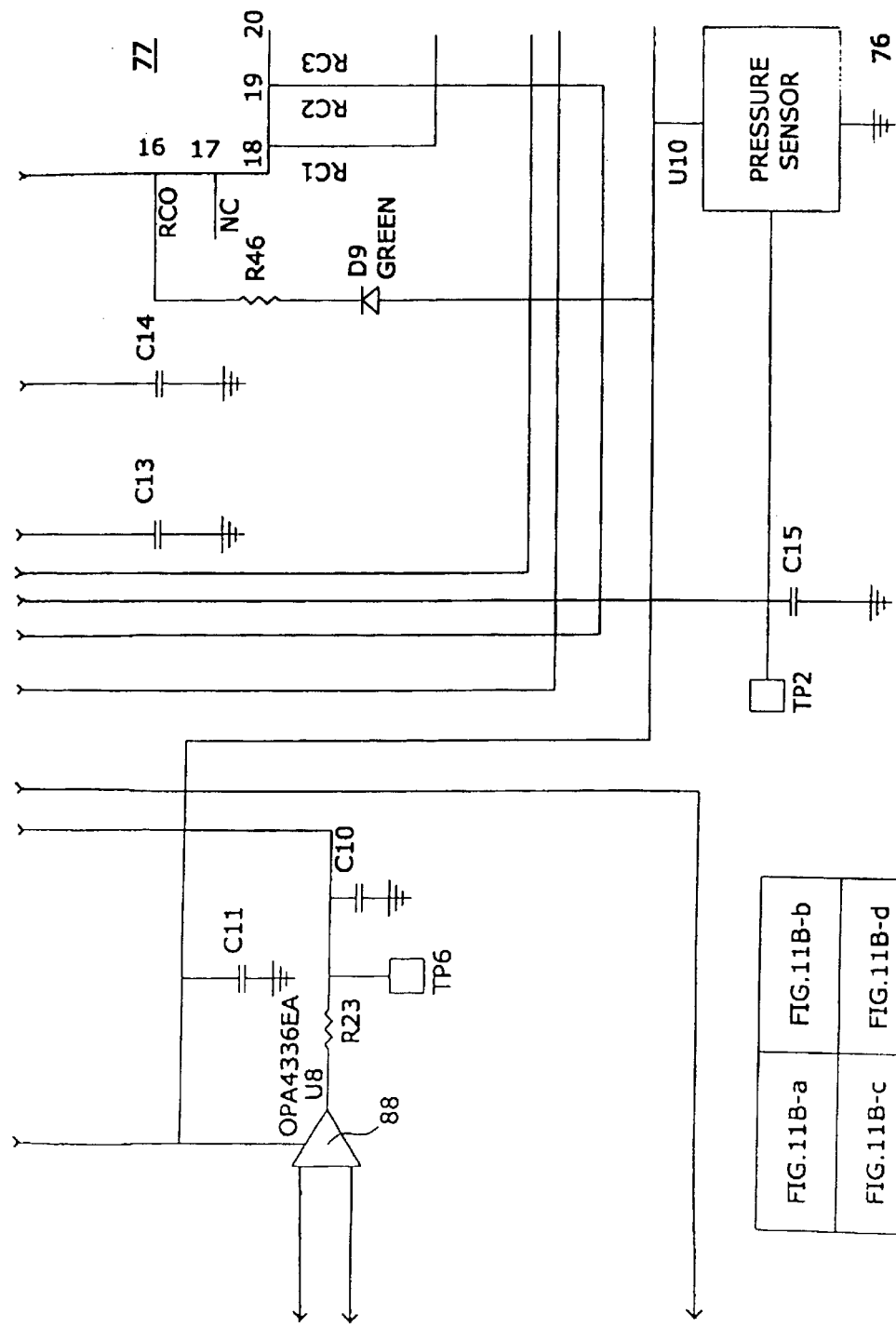
FIG.11B-d

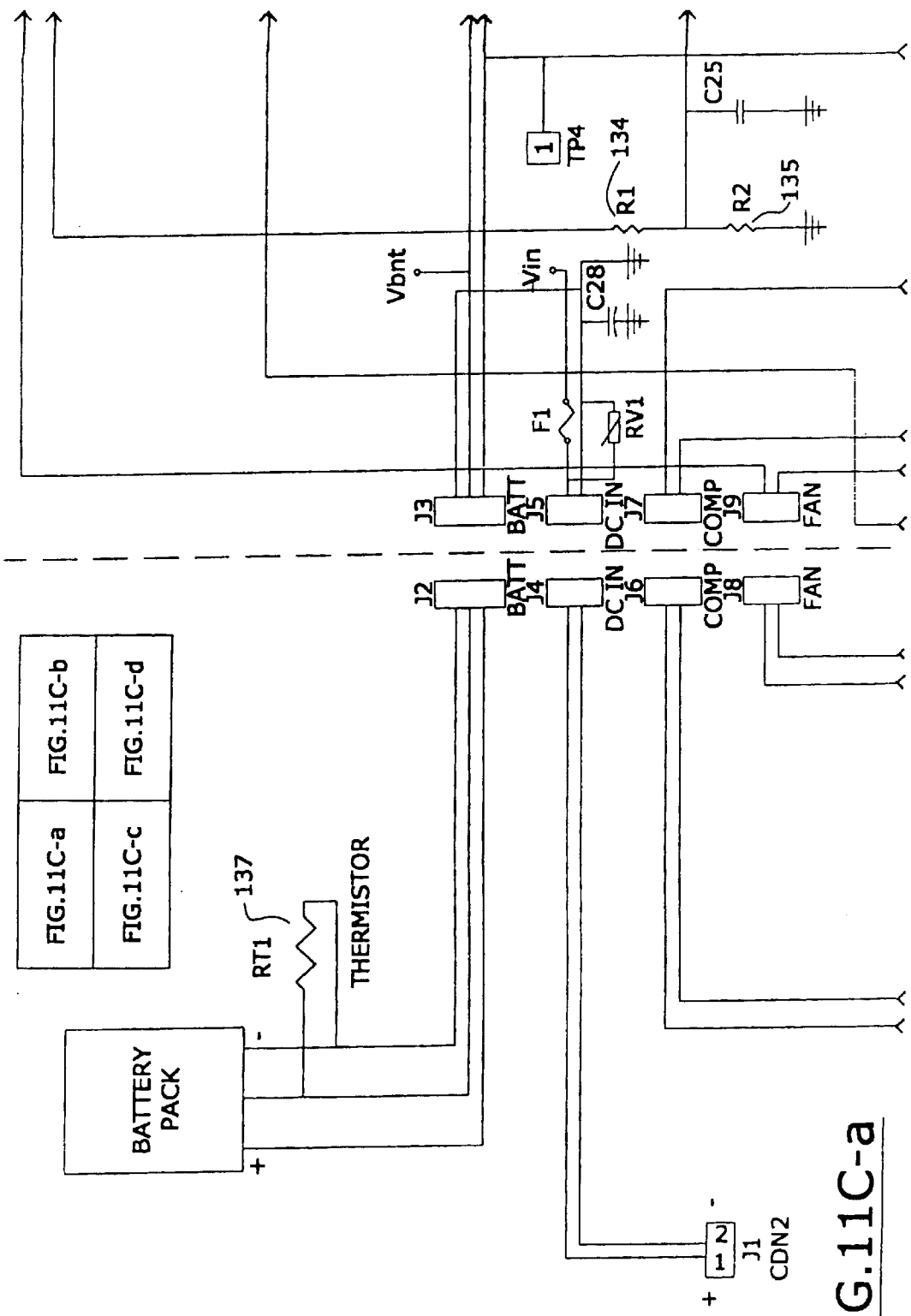
FIG.11C-a

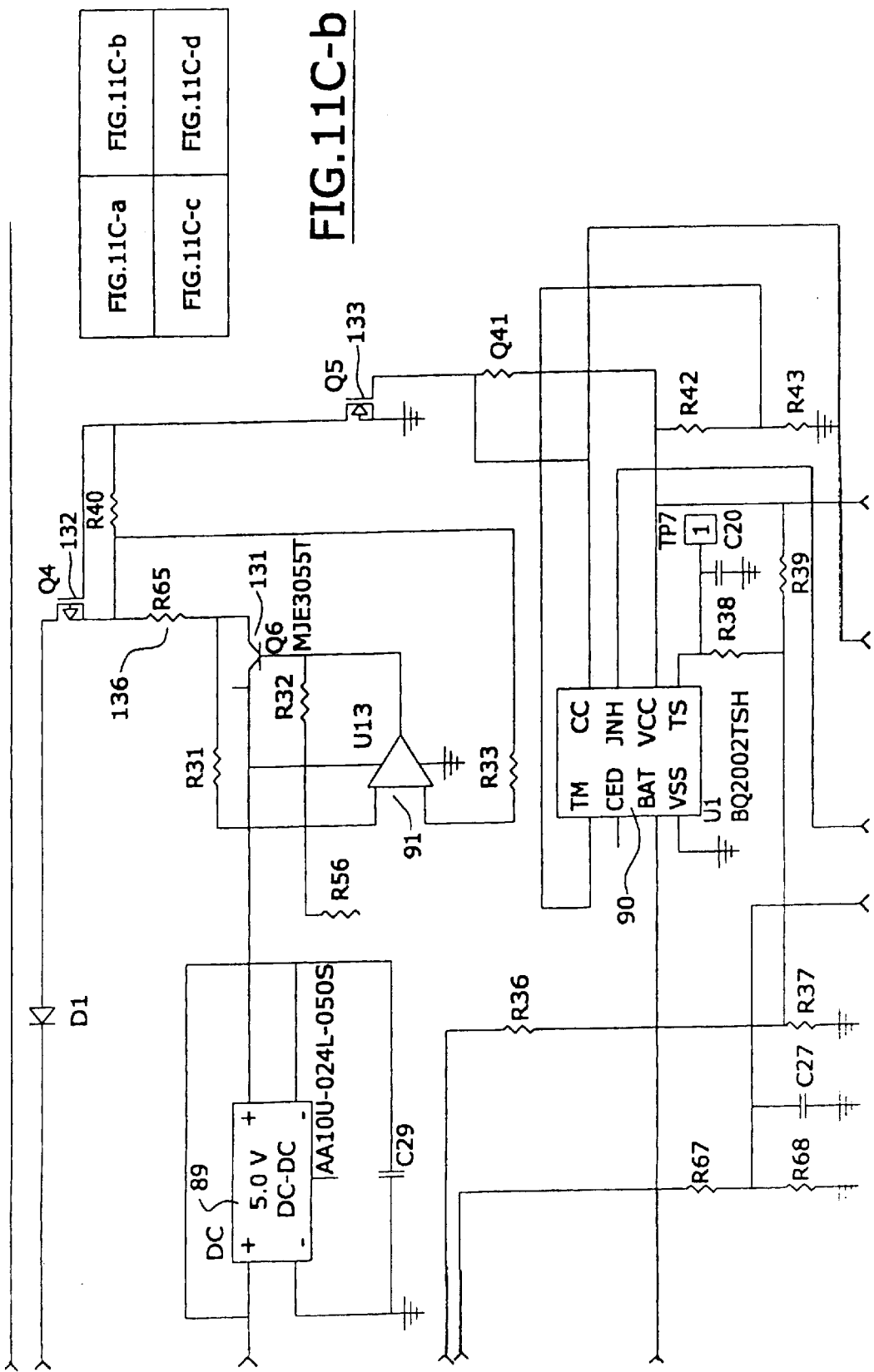

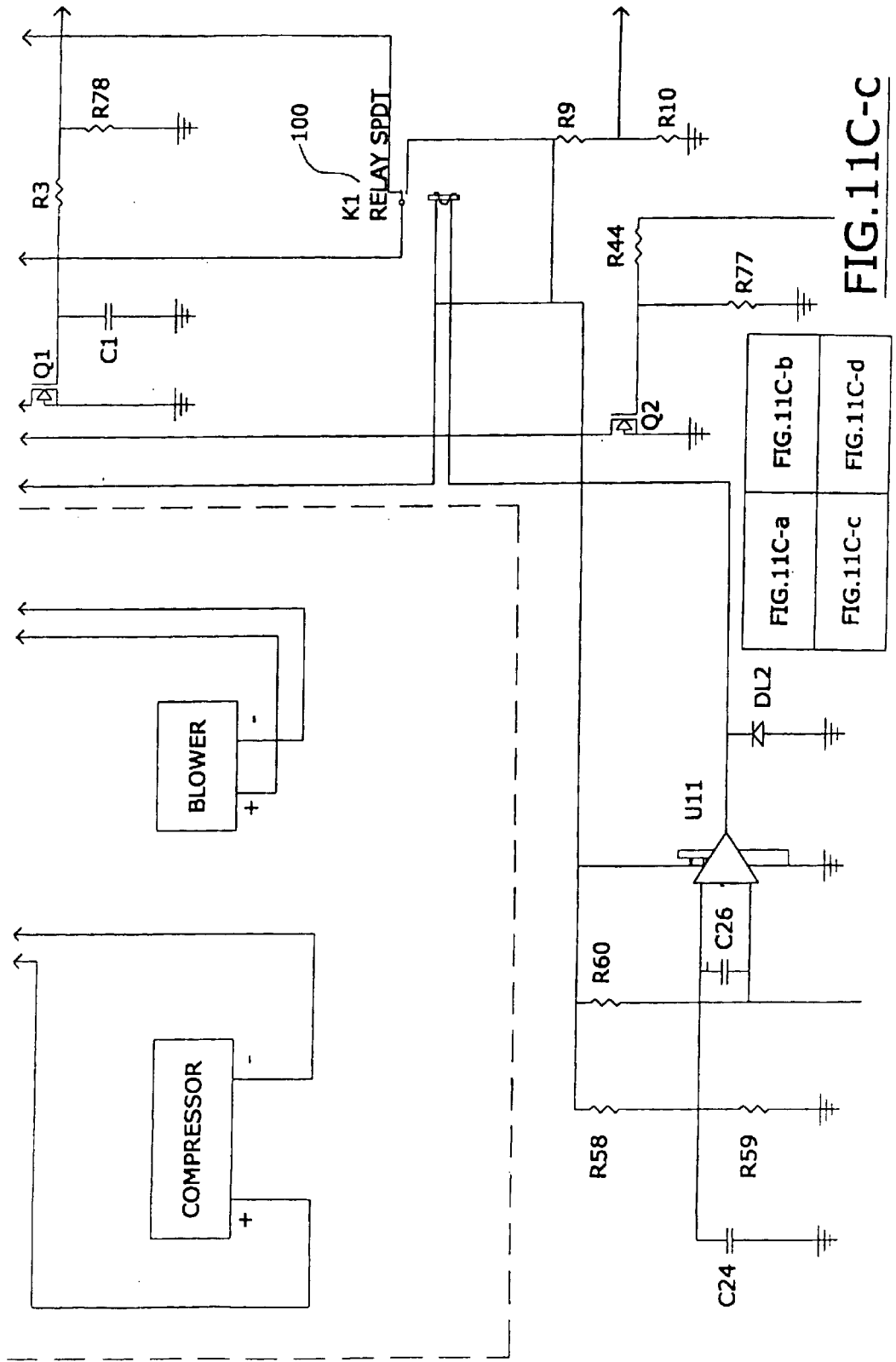
FIG.11C-c

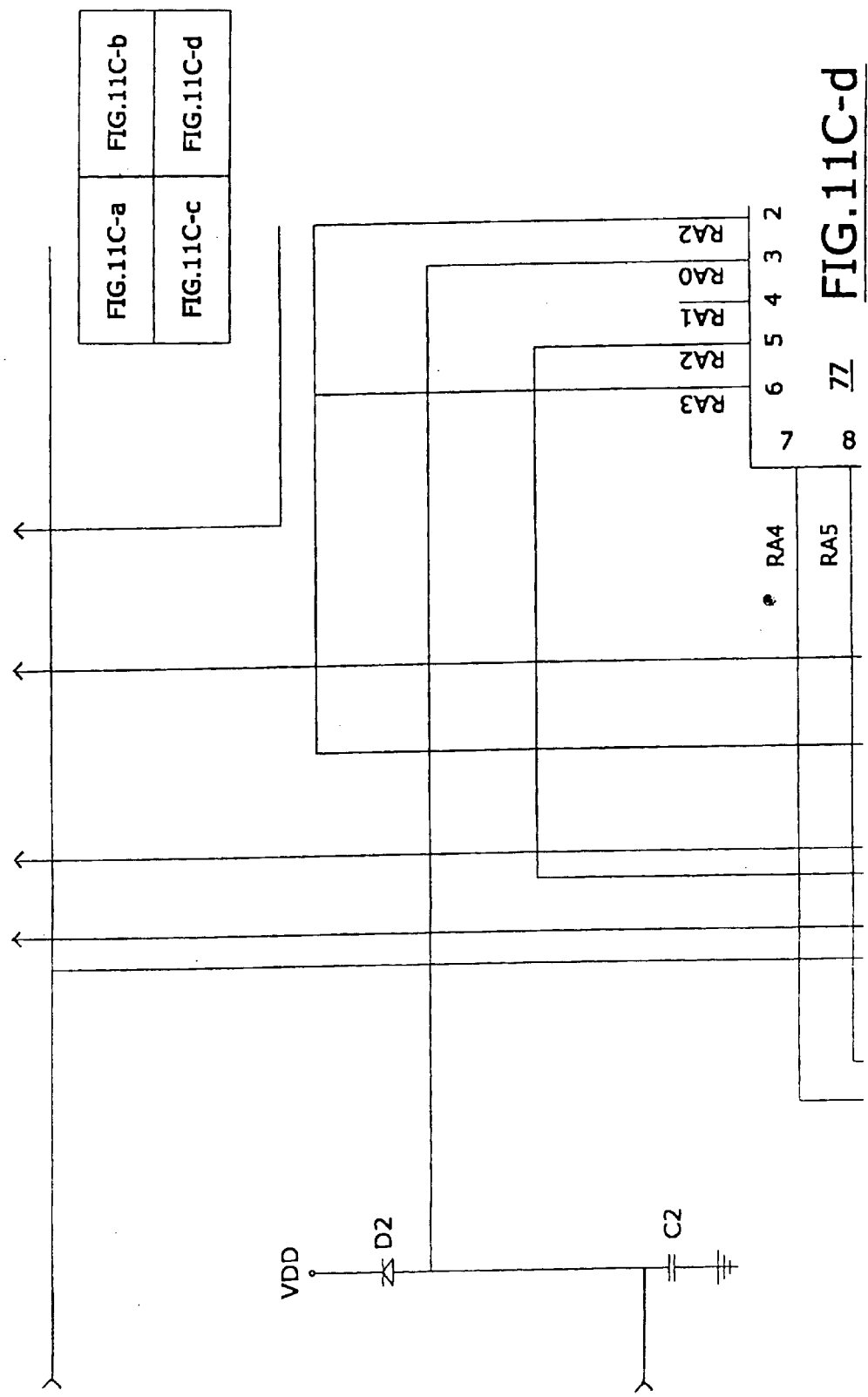

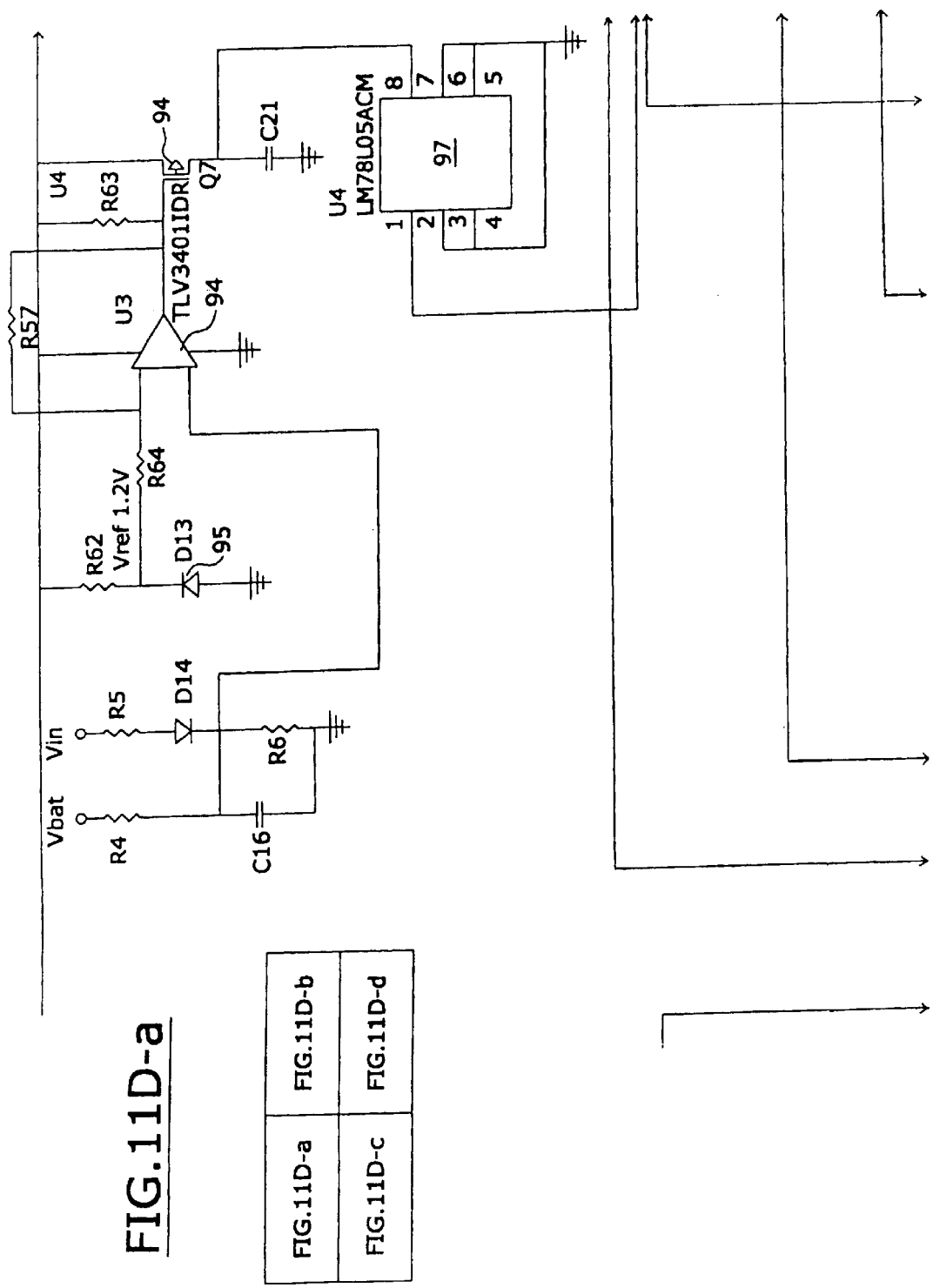
FIG.11D-a

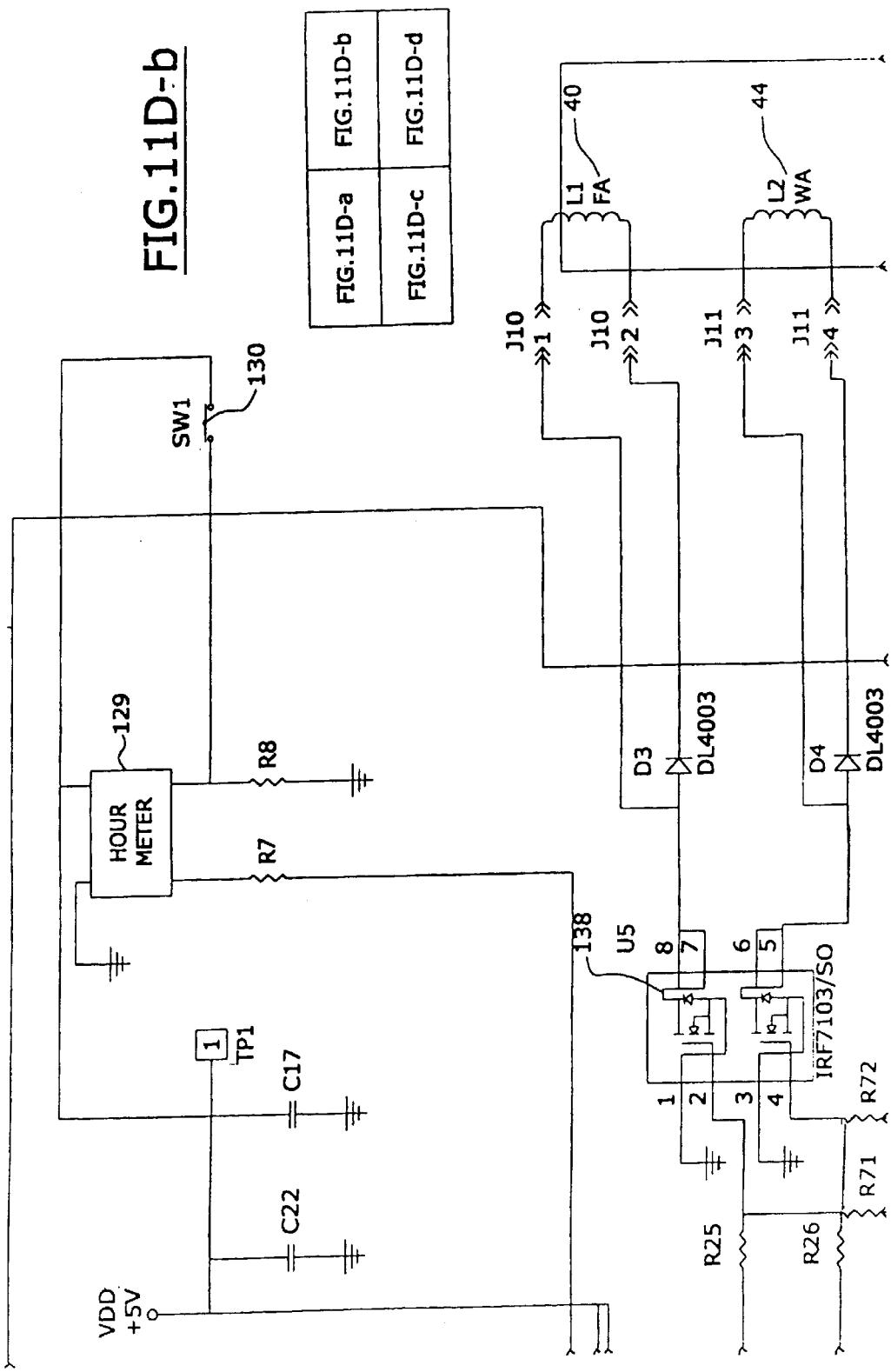
FIG.11D-b

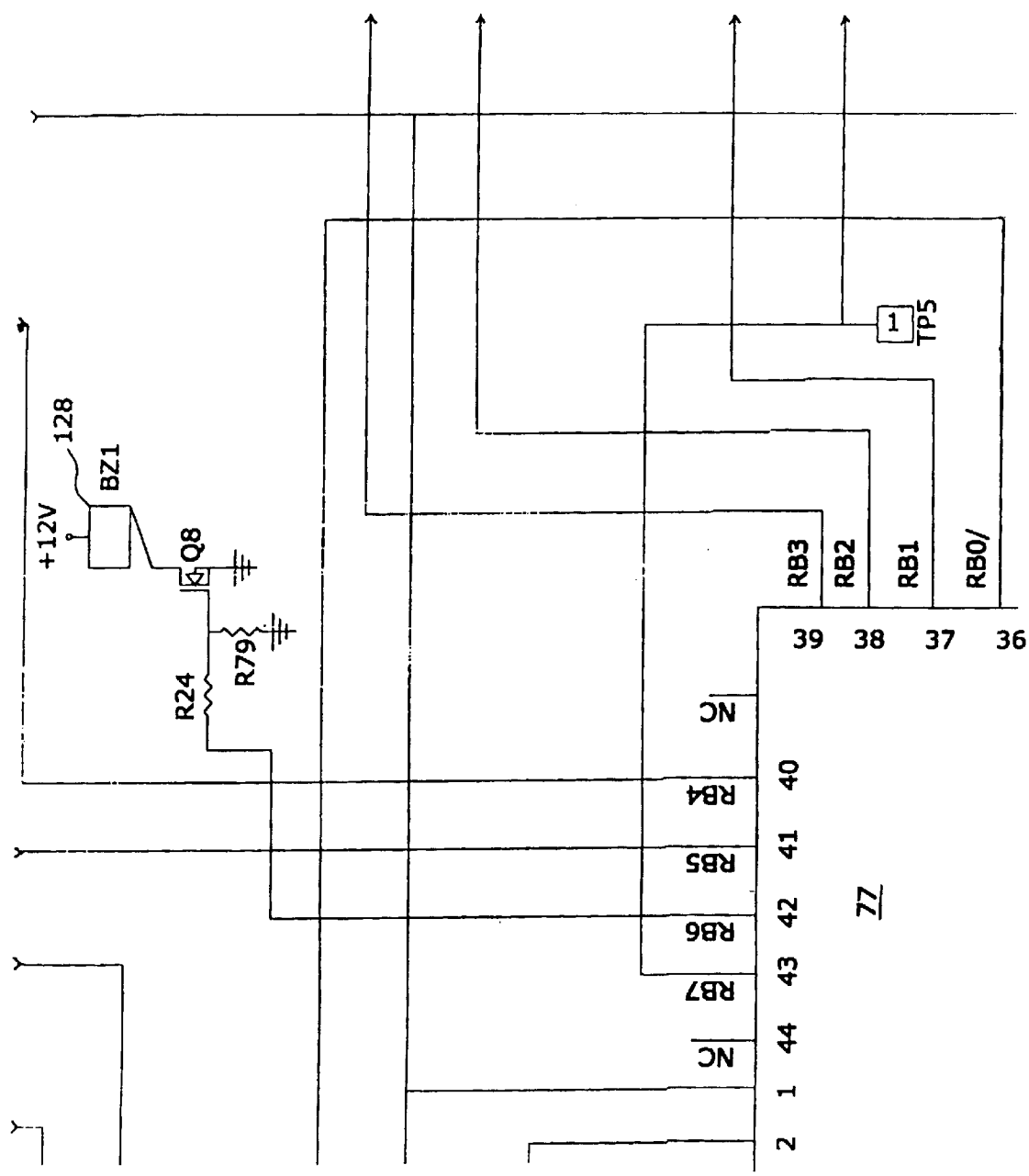
FIG.11D-c

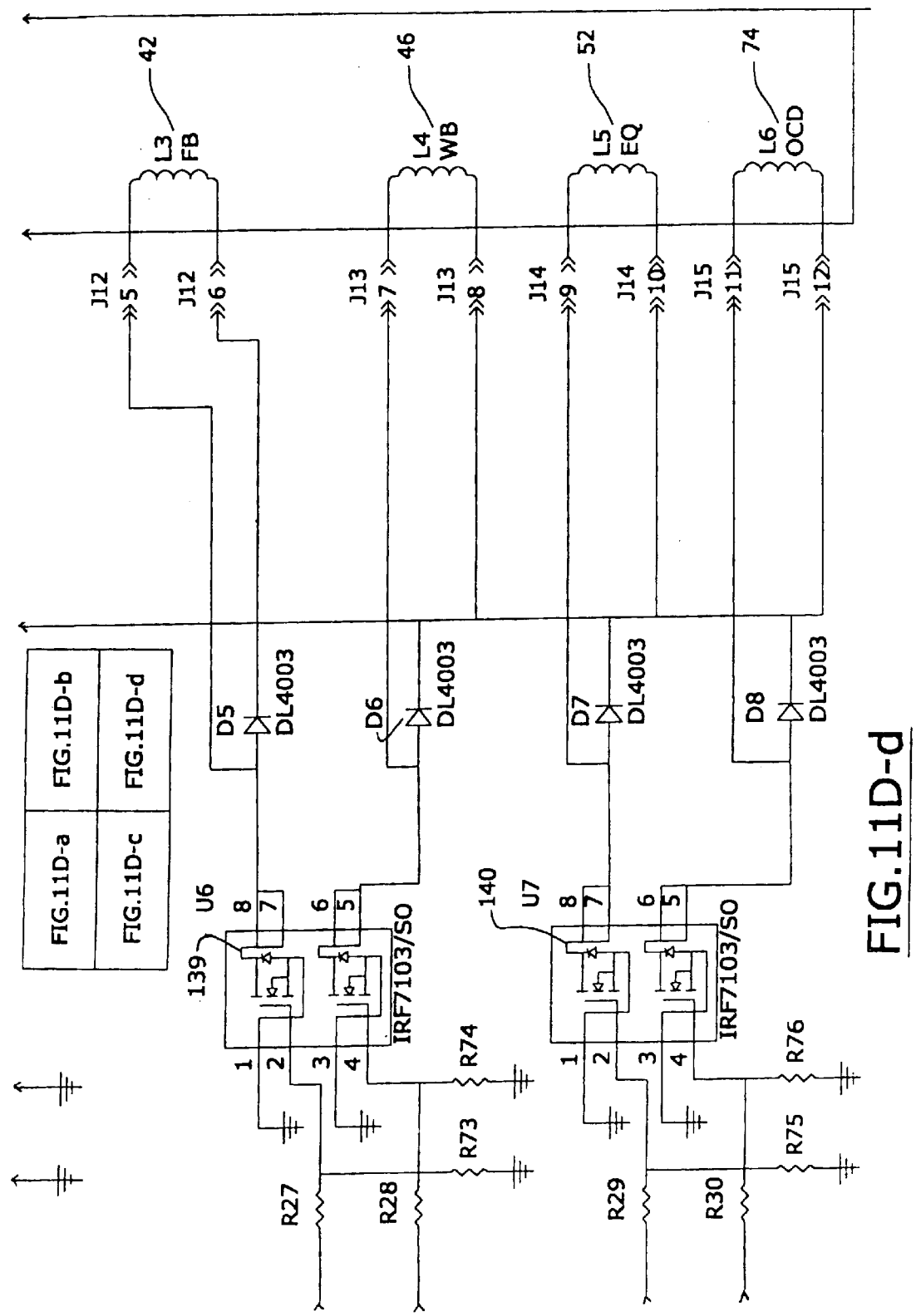
FIG.11D-d

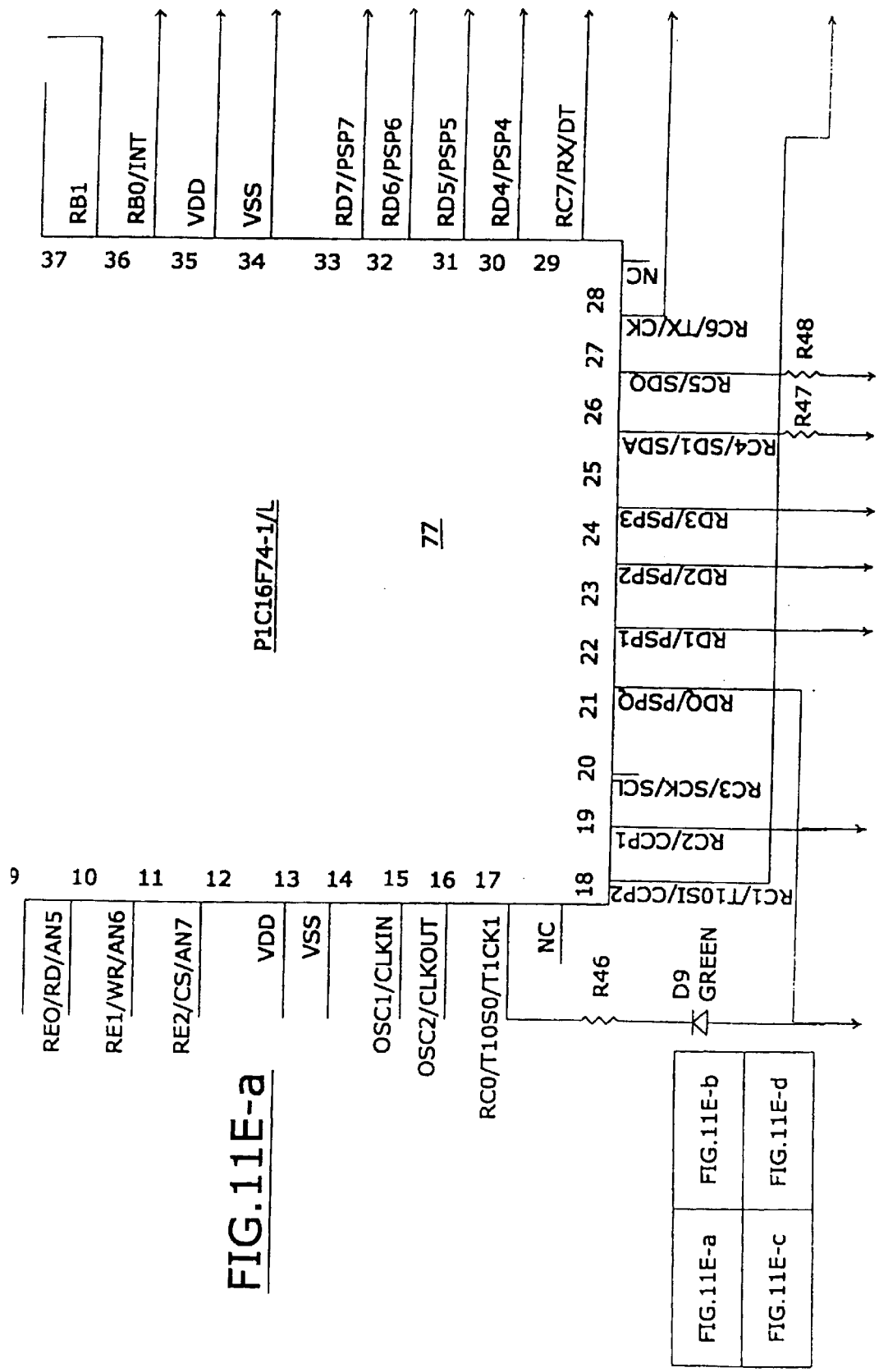
FIG.11E-a

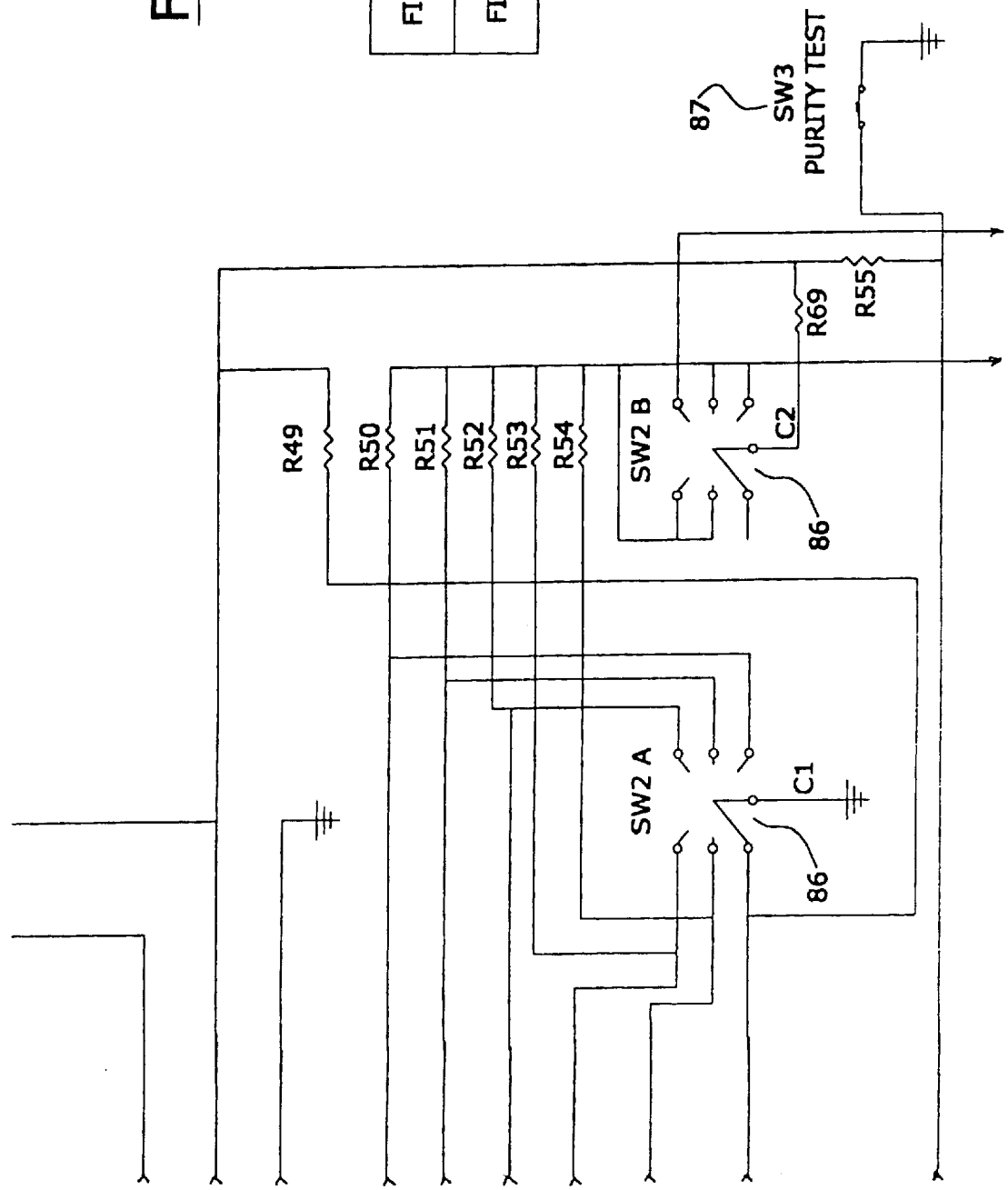

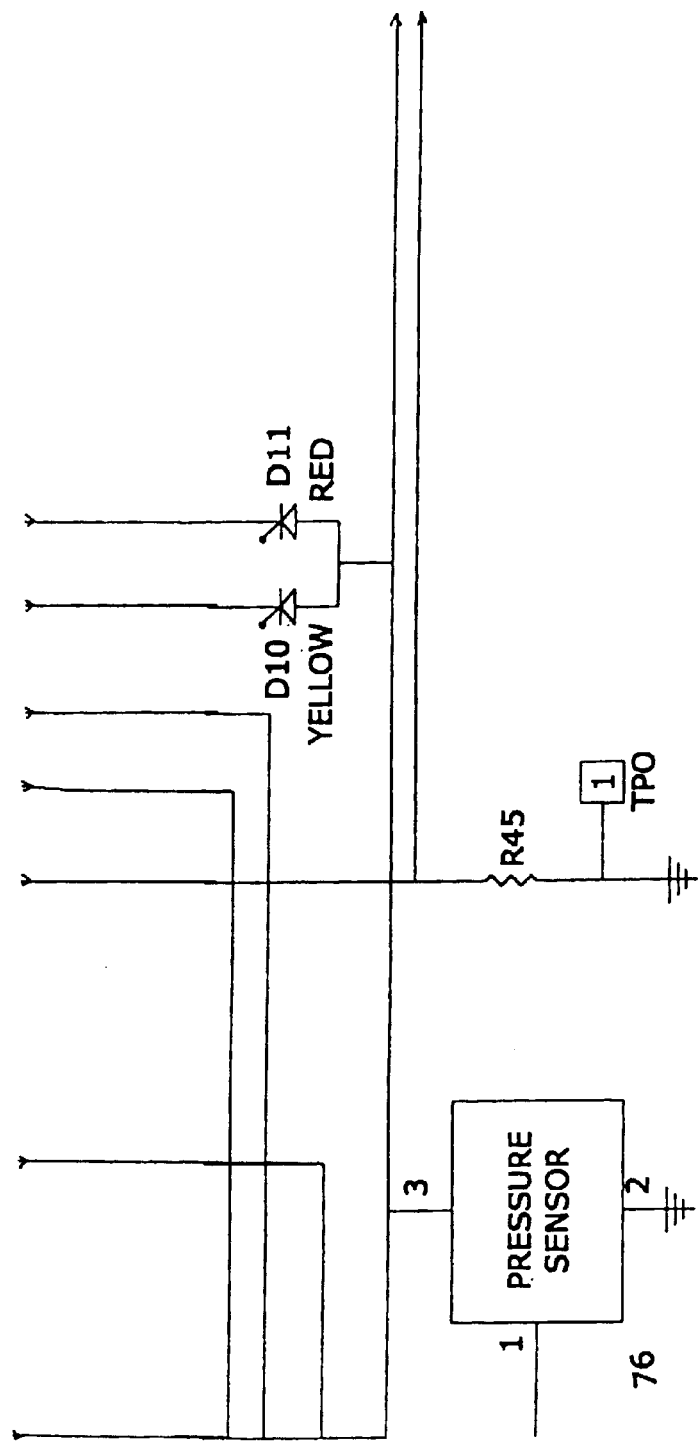
FIG.11E-c

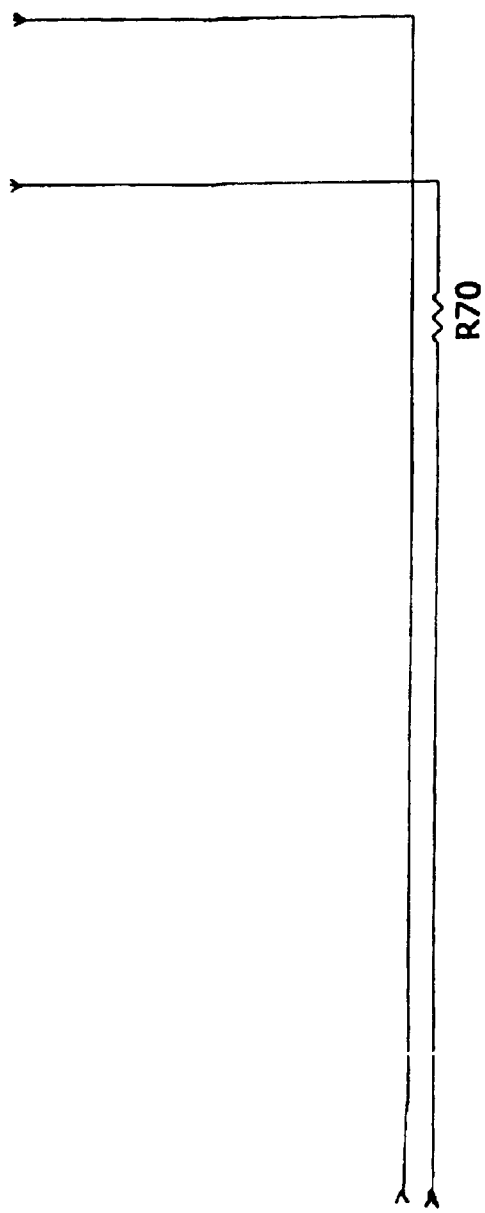
FIG.11E-d

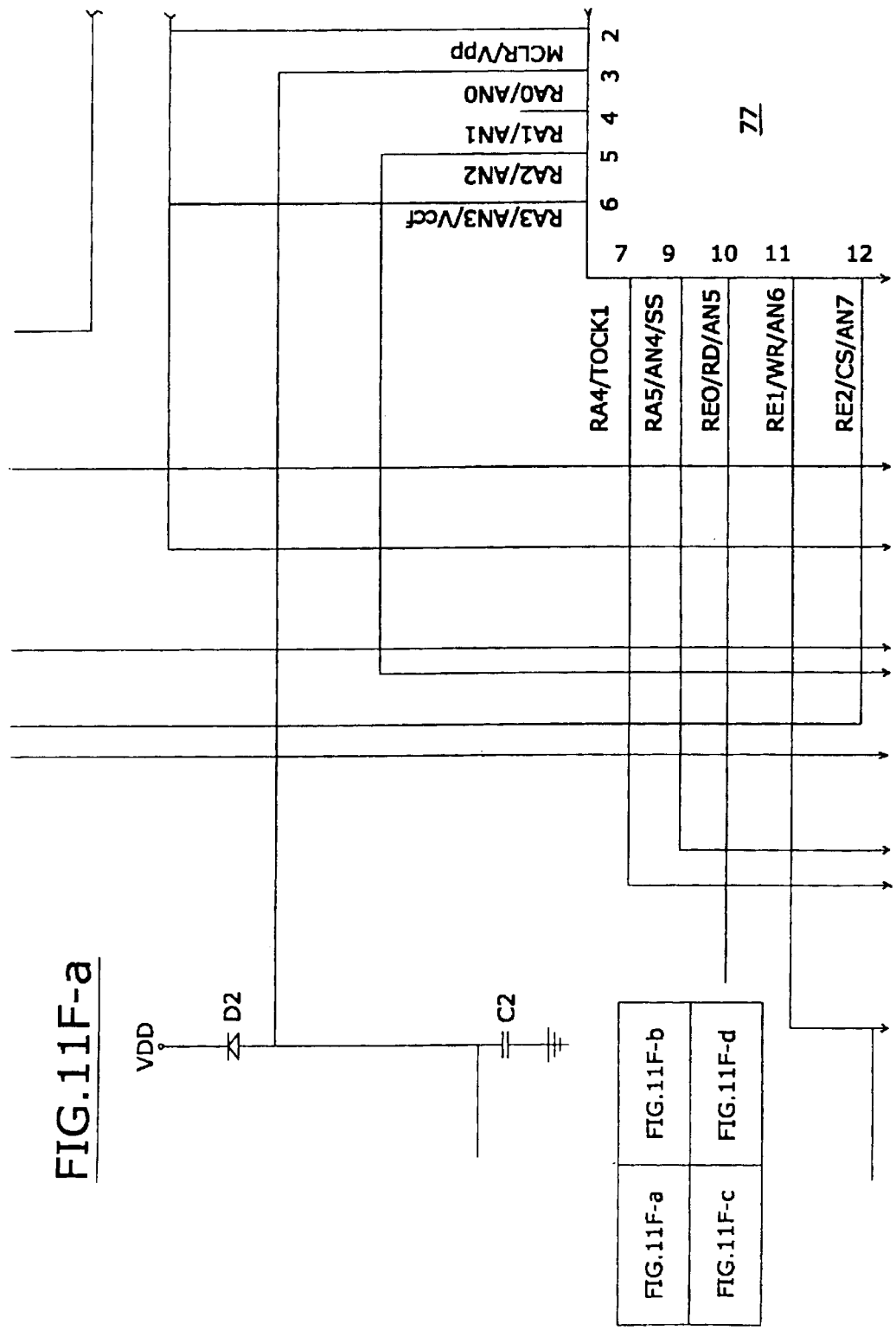
FIG.11F-a

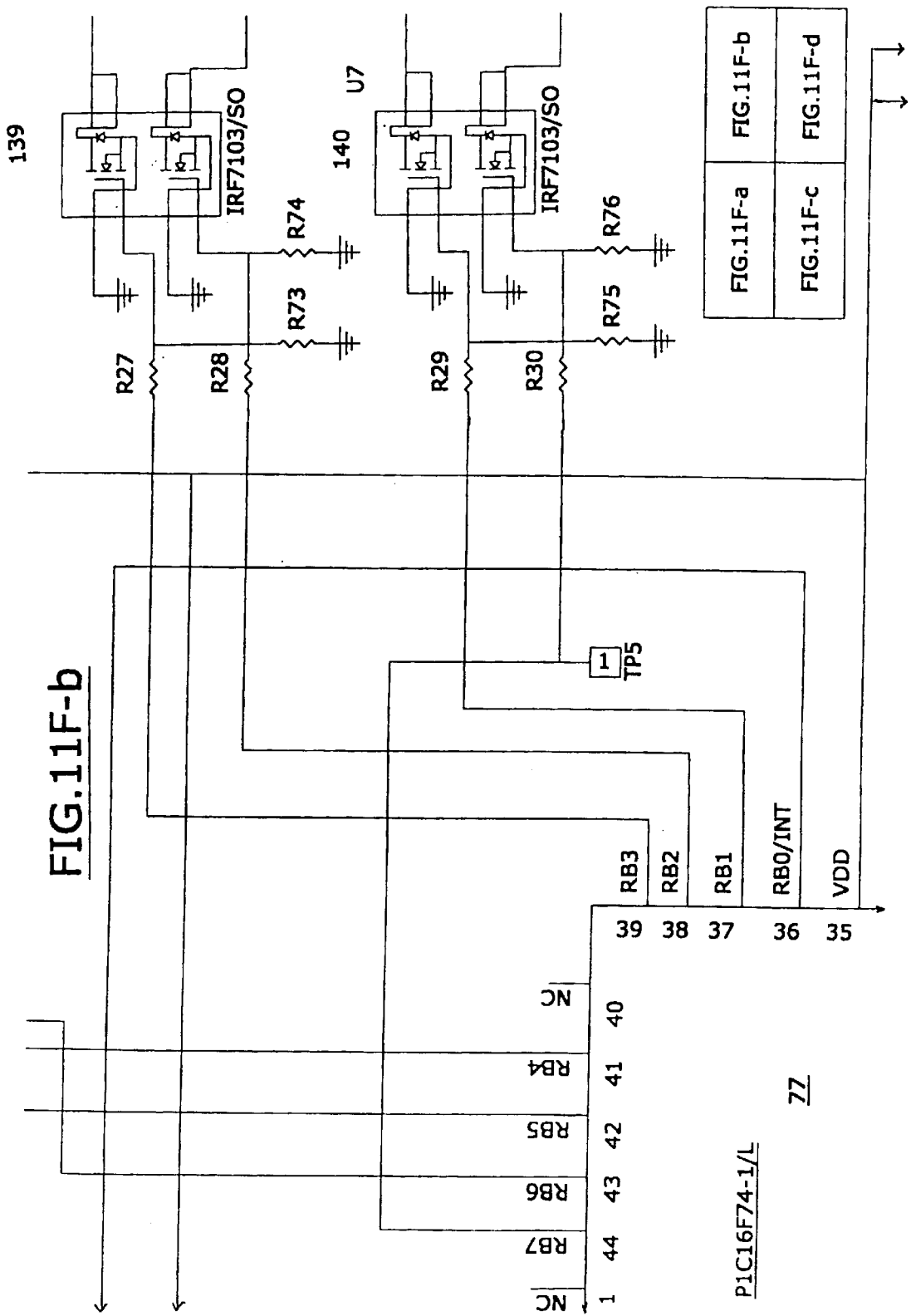

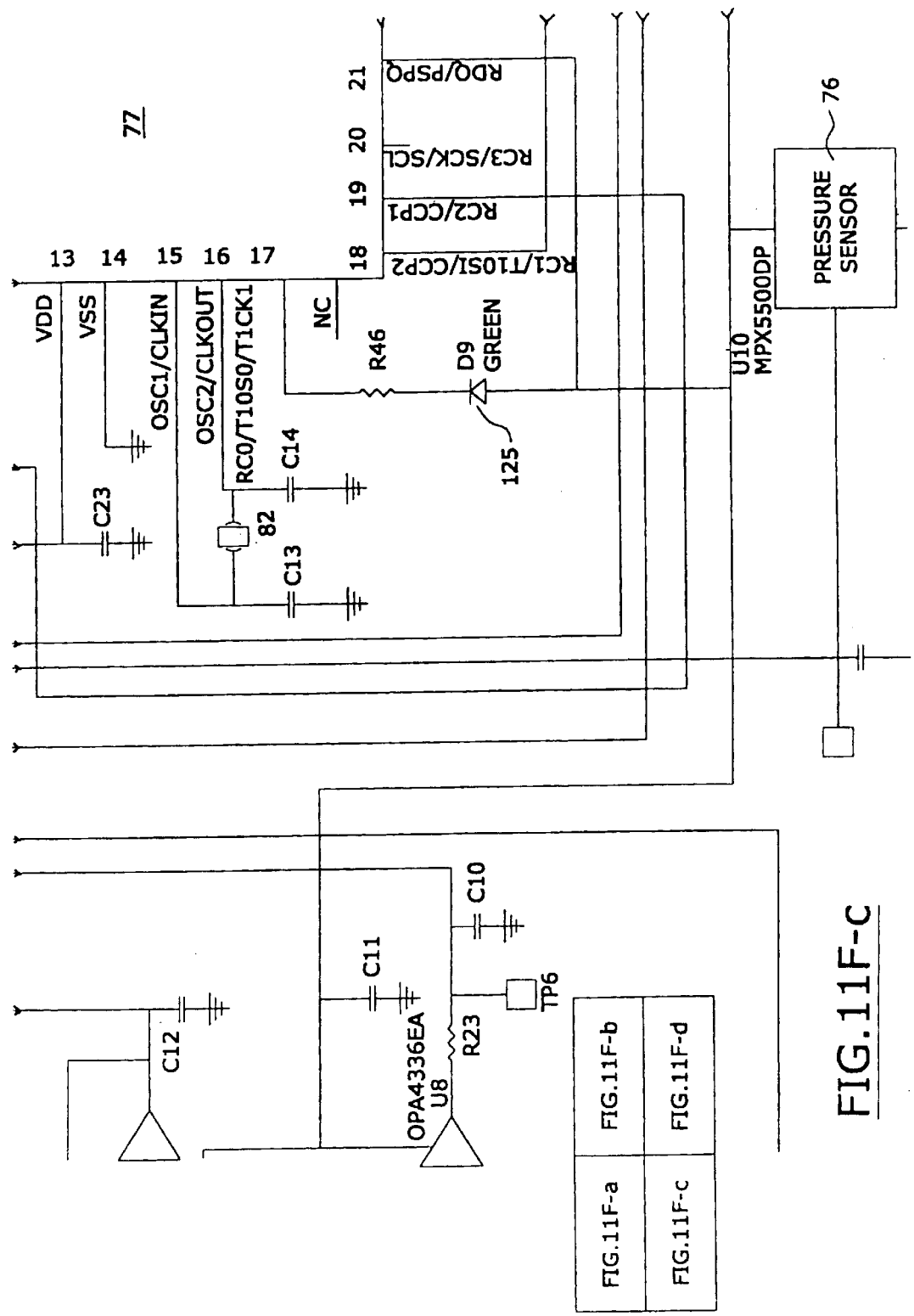
FIG.11F-c

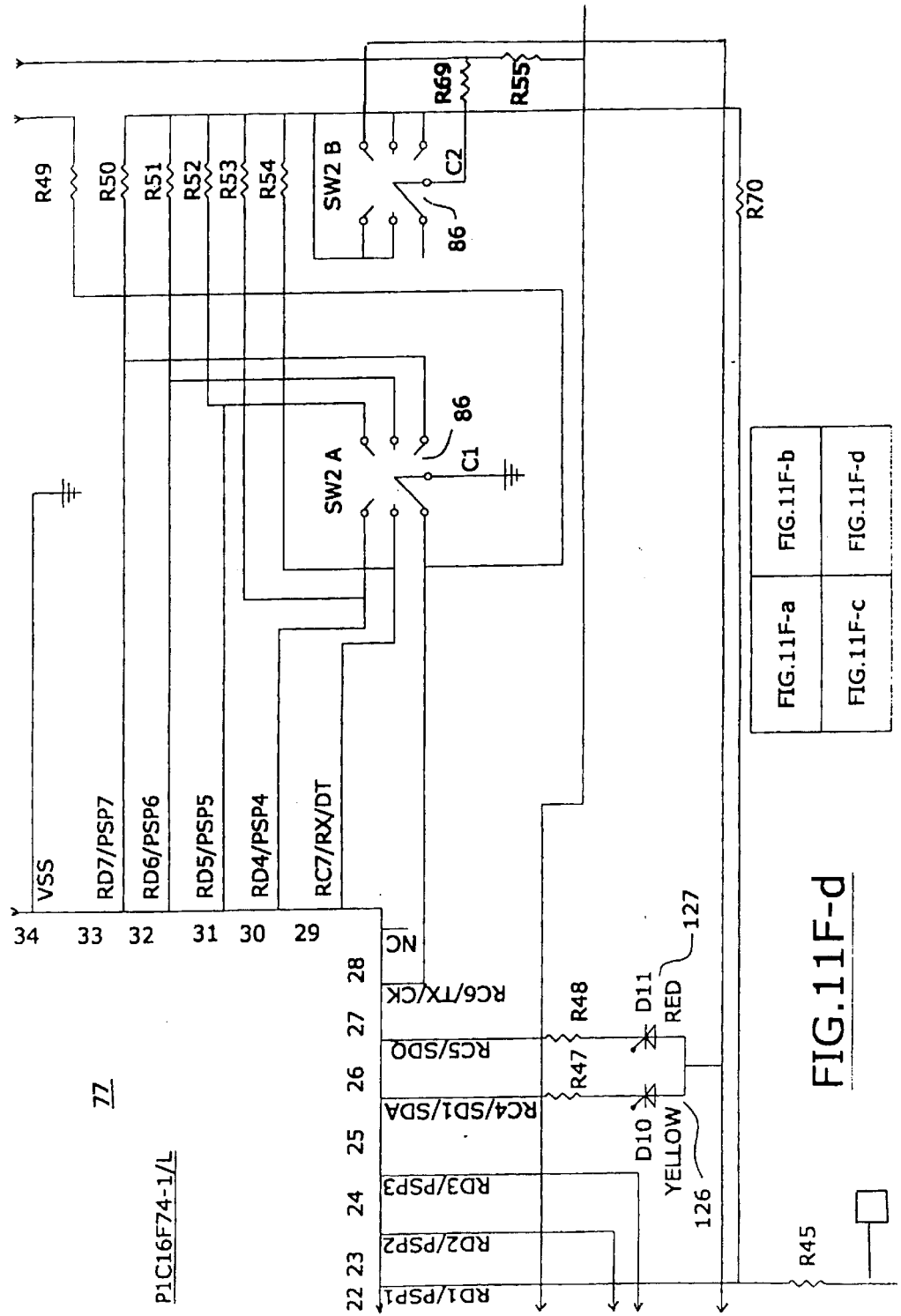
FIG.11F-d

PORTABLE OXYGEN CONCENTRATOR

CROSS-REFERENCE TO RELATED APPLICATIONS

This application claims benefit to U.S. provisional application serial No. 60/353,563, filed Jan. 31, 2002.

This invention relates generally to gas concentration apparatus for separating gas mixtures by pressure swing adsorption ("PSA") and more particularly to PSA apparatus intended to deliver oxygen for medical use.

BACKGROUND OF THE INVENTION

The general type and operating principles of PSA, or pressure swing adsorption, apparatus with which this invention is concerned are described in U.S. Pat. Nos. 3,564,816; 3,636,679; 3,717,974; 4,802,899; 5,531,807 and 5,871,564, among others. For example, a pressure swing adsorption apparatus may include one or more adsorbers, each having a fixed sieve bed of adsorbent material to fractionate at least one constituent gas from a gaseous mixture by adsorption into the bed, when the gaseous mixture from a feed stream is sequentially directed through the adsorbers in a co-current direction. While one adsorber performs adsorption, another adsorber is simultaneously purged of its adsorbed constituent gas by part of the product gas that is withdrawn from the first or producing adsorber and directed through the other adsorber in a counter-current direction. Once the other adsorber is purged, the feed stream at a preset time is then directed to the other adsorber in the co-current direction, so that the other adsorber performs adsorption. The first adsorber then is purged either simultaneously, or in another timed sequence if there are more than two adsorbers, all of which will be understood from a reading of the above described patents.

When, for example, such apparatus is used to produce a high concentration of oxygen from ambient air for use in various applications, whether medical, industrial or commercial, air which enters the apparatus typically contains about 78% nitrogen, 21% oxygen, 0.9% argon, and a variable amount of water vapor. Principally, most of the nitrogen is removed by the apparatus to produce a gas product, which for medical purposes, for example, typically may contain at least about 80% oxygen. Most such apparatus for medical uses generally are too bulky for use by patients who are traveling or otherwise wish to leave their home environments for any purpose. In those cases, patients will normally forego the use of oxygen concentrators and revert to the use of pressurized oxygen tanks. While oxygen tanks have been very useful in enabling patients to be more ambulatory, they nevertheless are restricted in use, as for example because of limited oxygen storage capacity or because their use may be prohibited in certain modes of public transportation or locations where flammable materials can create a hazard. Although the useful life of oxygen tanks may be extended by the use of oxygen concentration devices ("OCD"), as disclosed, for example, in co-pending U.S. application Ser. No. 09/420,826, filed Oct. 19, 1999, their use nevertheless continues to be problematic because of safety and storage concerns, access to re-supplies of oxygen, and continuing medical expenses and reimbursement paperwork for the oxygen.

SUMMARY OF THE INVENTION

The present invention provides a new and improved pressure swing adsorption ("PSA" or "oxygen concentrator") apparatus that can attain the required concentrations of oxygen for the desired application(s), yet be highly portable and easily manipulated and transported even by patients with relatively limited physical capacities. This is accomplished by a unique configuration combining an inventive PSA design with an oxygen conservation device ("OCD") for pulse dose application of oxygen from the PSA to the user.

The intended use of the apparatus is to deliver supplemental, high-purity oxygen to persons who suffer, for example, from various forms of Chronic Obstructive Pulmonary Disease (COPD). The invention preferably uses a two-bed PSA together with an integrated OCD to provide oxygen in doses up to an equivalent of about 5 liters per minute (LPM) effective rate of continuous high-concentration oxygen at concentrations over 90%.

BRIEF DESCRIPTION OF THE DRAWING

The foregoing and other objects, features and advantages of the invention will become more apparent from a reading of the following description in connection with the accompanying drawing of a preferred embodiment of the invention, in which:

FIGS. 11A, 11B-a through d, 11C-a through d, 11D-a through d, 11E-a through d, and 11F-a through d are diagrams of the electronic circuit used to control the components of the preferred embodiment;

DETAILED DESCRIPTION OF THE PREFERRED EMBODIMENT

Figure 1:
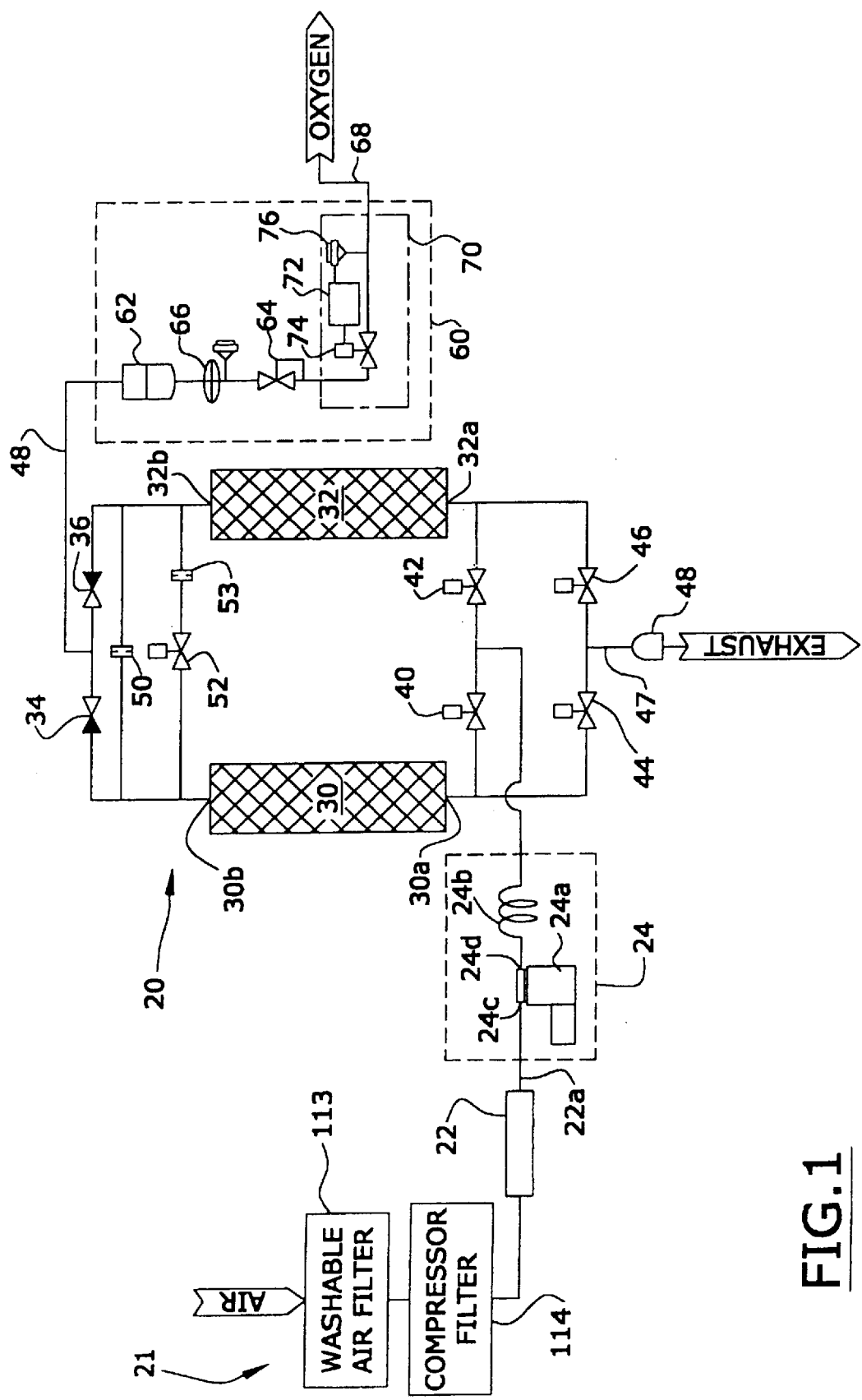
FIG. 1 is a schematic illustration of a combined PSA/OCD apparatus according to the invention.

Turning now to the drawing and in accordance with the present invention, there is shown a preferred embodiment, generally indicated as 20, of a combined pressure swing adsorption apparatus and oxygen conserving device, or PSA/OCD, used for fractionating at least one component, namely nitrogen, from a gaseous mixture, generally but not necessarily ambient air, by pressure swing adsorption to produce a product gas, and for delivering the product gas at specific and variable intervals upon demand by a user. The general operating principles of pressure swing adsorption are well known and are disclosed, for example, in commonly assigned U.S. Pat. Nos. 4,802,899, 5,531,807 and 5,871,564, the entire disclosures of which are incorporated by reference herein. Similarly, conservation by pulse dosing of the supply of a product gas such as oxygen from a pressurized tank, in order to increase the useful life of the stored oxygen, also is generally known and is disclosed, for example, in co-pending U.S. application Ser. No. 09/420,826 filed Oct. 19, 1999, the entire disclosure of which also is incorporated by reference herein.

With reference to FIG. 1, ambient air is supplied to the PSA/OCD apparatus 20 through a filtered intake 21 and an intake resonator 22 to decrease the noise from the intake of the ambient air feed stream. The feed stream continues from resonator 22 and is moved from its outlet 22a by a feed air compressor/heat exchanger assembly 24 alternatively to first and second adsorbers 30, 32 through feed valves 40 and 42 respectively. Compressor/heat exchanger assembly 24 as shown includes a compressor 24a with an air inlet 24c and an outlet 24d followed by the heat exchanger 24b.

When the feed stream alternatively enters inlets 30a, 32a of adsorbers 30, 32 in a co-current direction, the respective adsorber fractionates the feed stream into the desired concentration of product gas. The adsorbent material used for the beds to separate nitrogen from the ambient air may be a synthetic zeolite or other known adsorber material having equivalent properties.

The substantial or usable portion of the oxygen enriched product gas generated by the ambient air flowing in the co-current direction sequentially in each one of the adsorbers 30, 32 is directed through the outlet 30b, 32b and check valve 34, 36 of the corresponding adsorber to a product manifold 48 and then to a delivery control assembly 60, as will be described. The balance of the product gas generated by each adsorber is timed to be diverted through a purge orifice 50 and a properly timed equalization valve 52 and an optional flow restrictor 53 to flow through the other adsorber 30 or 32 in the counter-current direction from the respective outlet 30b, 32b and to the respective inlet 30a, 32a of the other adsorber to purge the adsorbed, primarily nitrogen, gases. The counter-current product gas and purged gases then are discharged to the atmosphere from the adsorbers through properly timed waste valves 44, 46, tubing 47 and a sound absorbing muffler 48.

Figure 2:
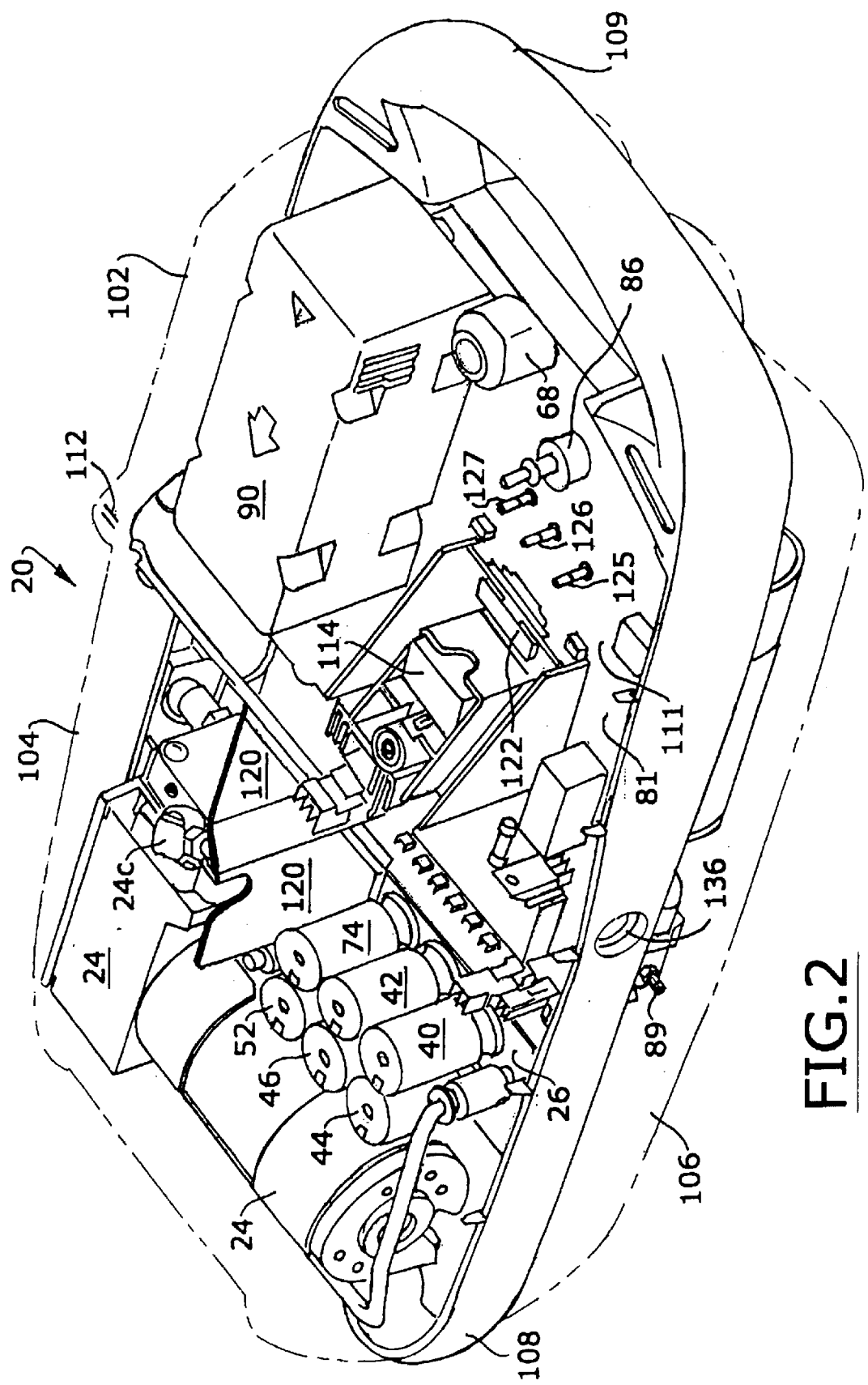
FIGS. 2 and 3 are perspective views, as viewed from the top, of a preferred embodiment of the invention with the upper and lower housing portions shown in phantom to highlight operating components of the invention.
Figure 3:
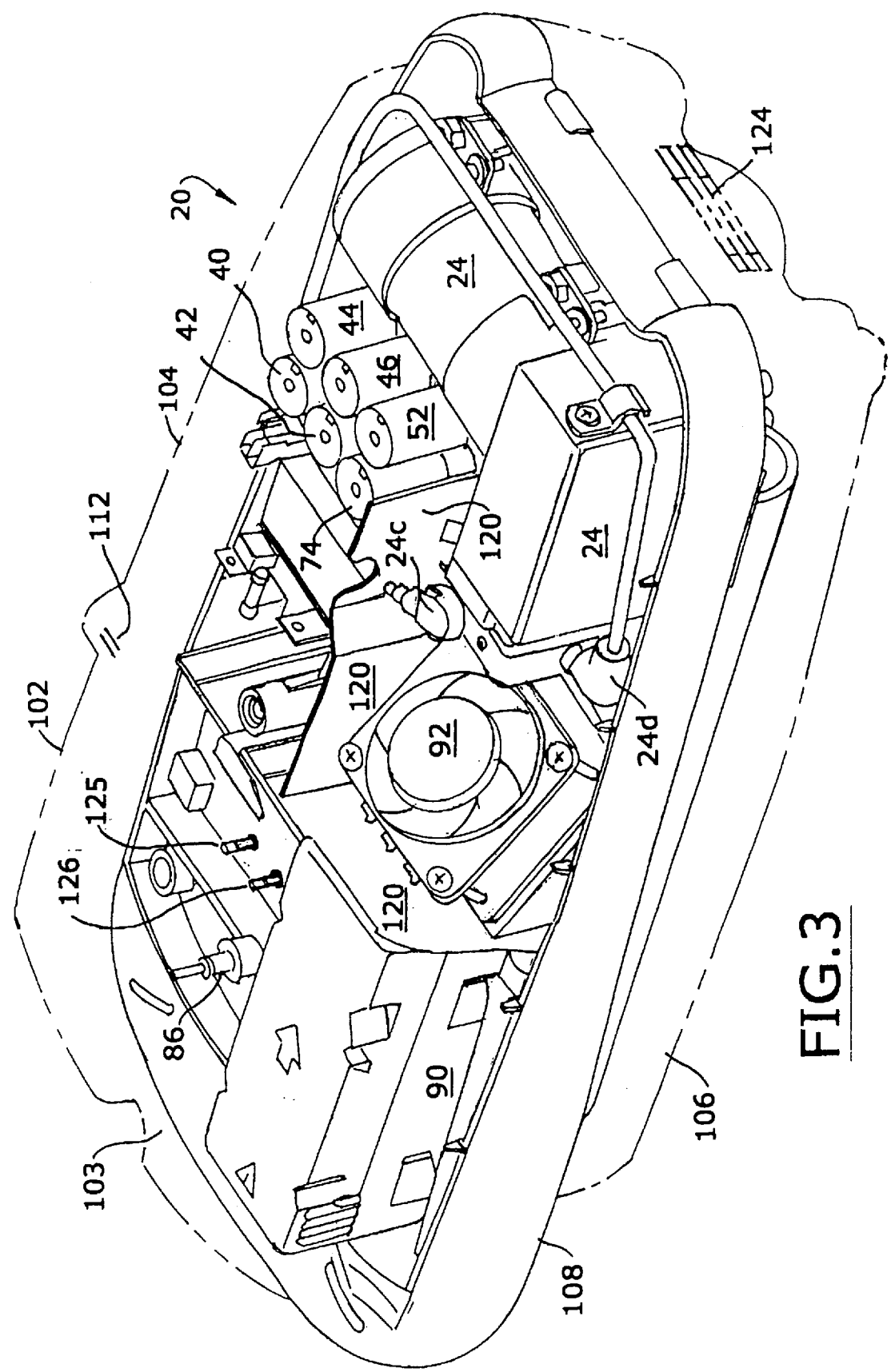
Figure 4:
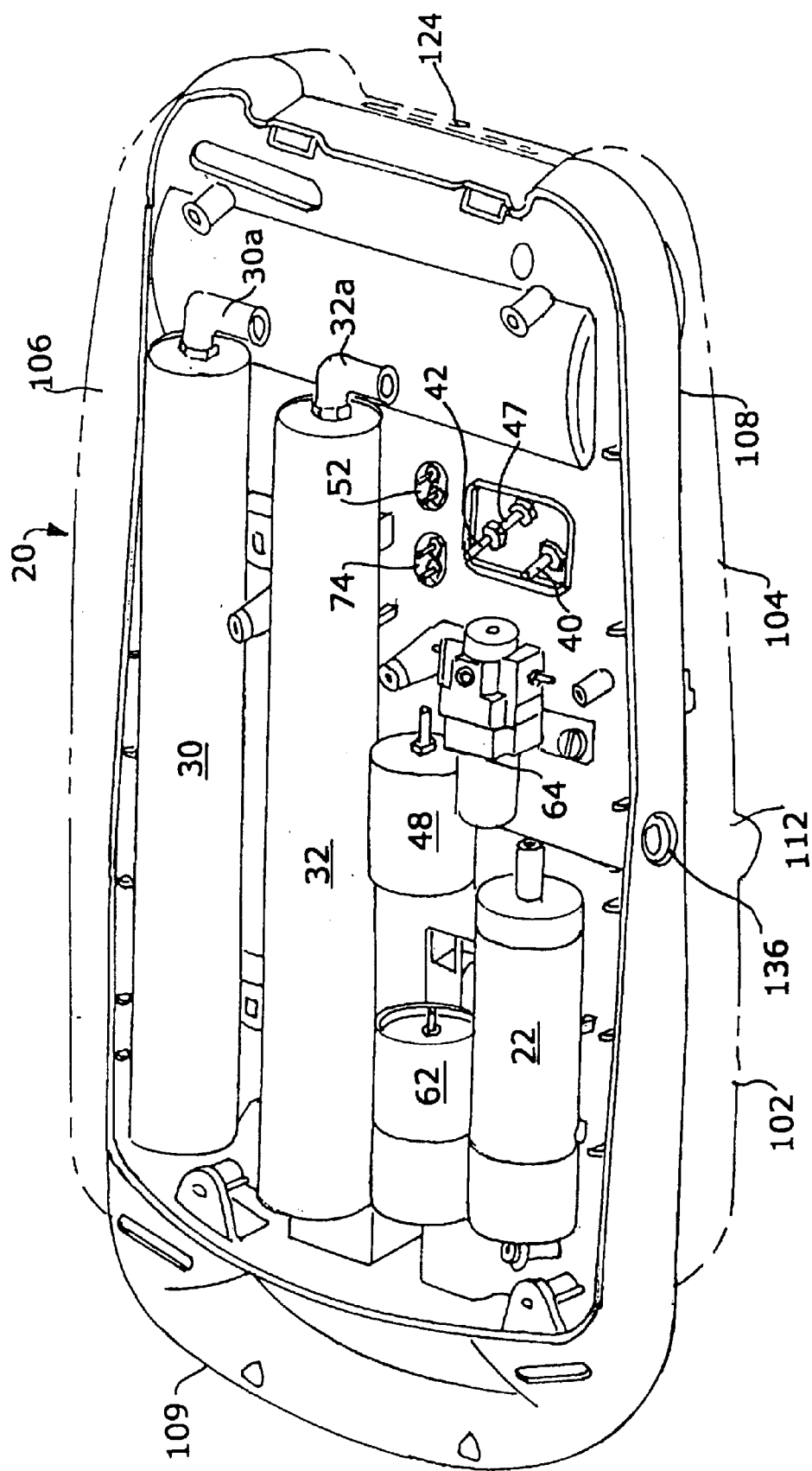
FIG. 4 is a similar prospective view, but as viewed from the bottom of the preferred embodiment.
Figure 5:
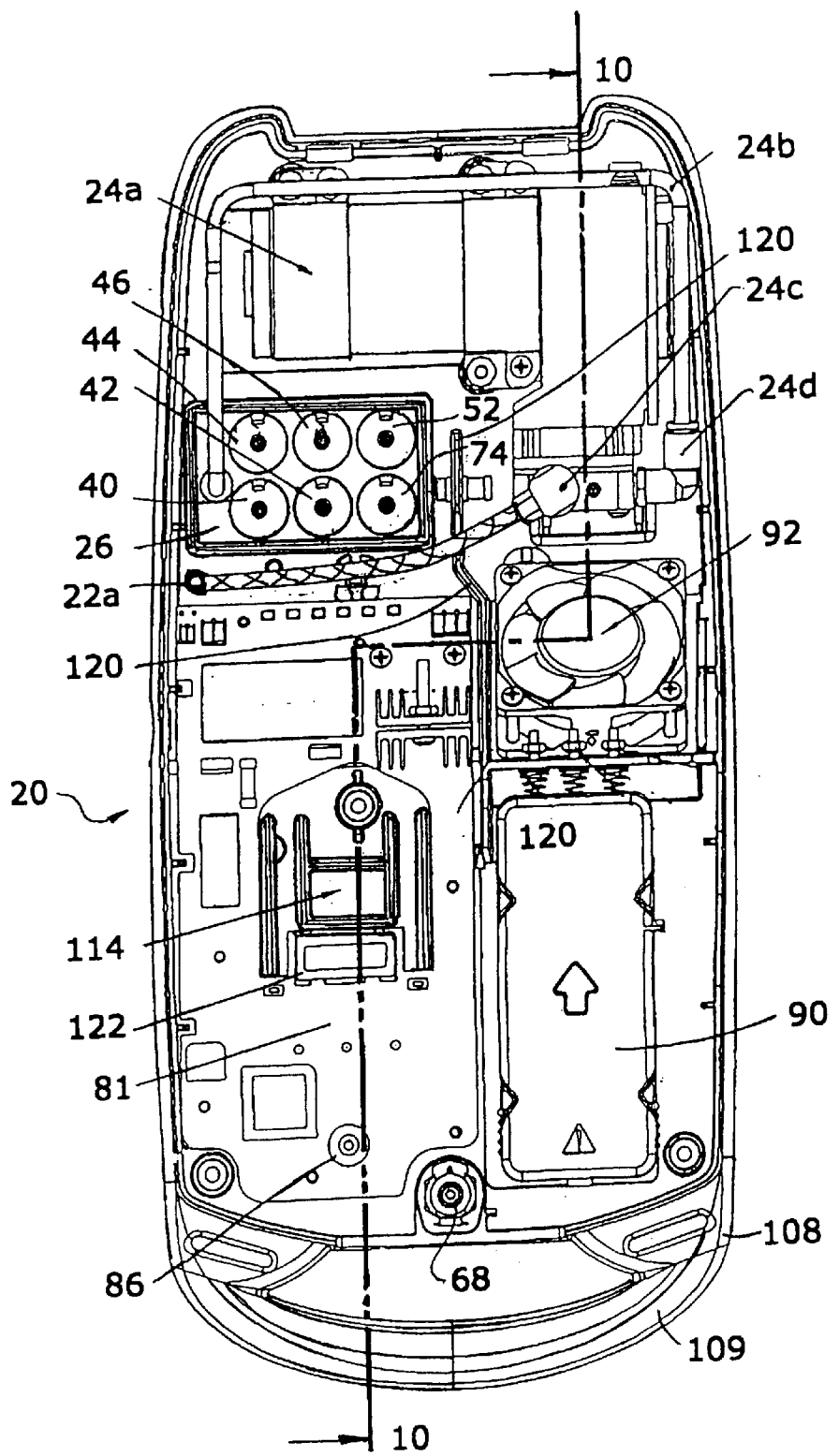
FIGS. 5, 6, 7, 8 and 9 are top, bottom, right side, left side and front views, respectively, of the preferred embodiment with the upper and lower housing portions removed.
Figure 6:
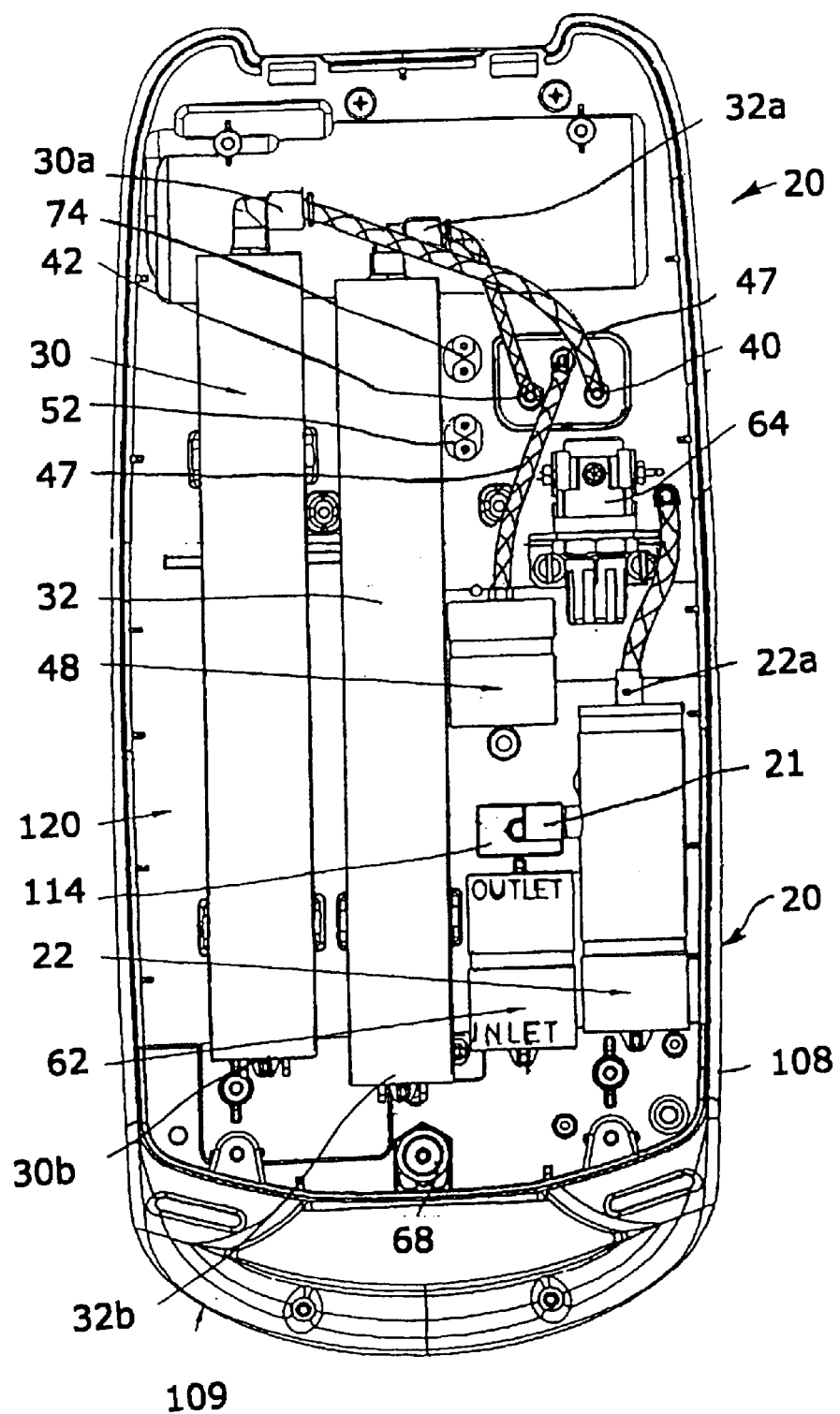
Figure 7:
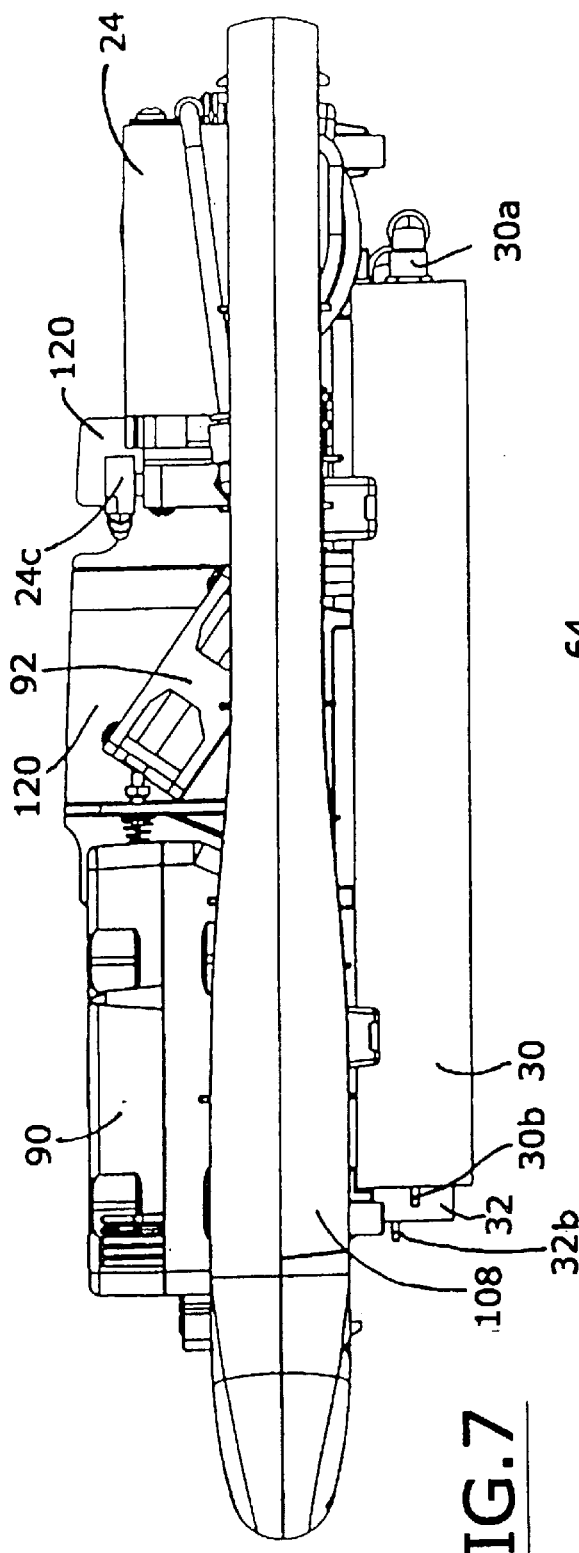
Figure 8:
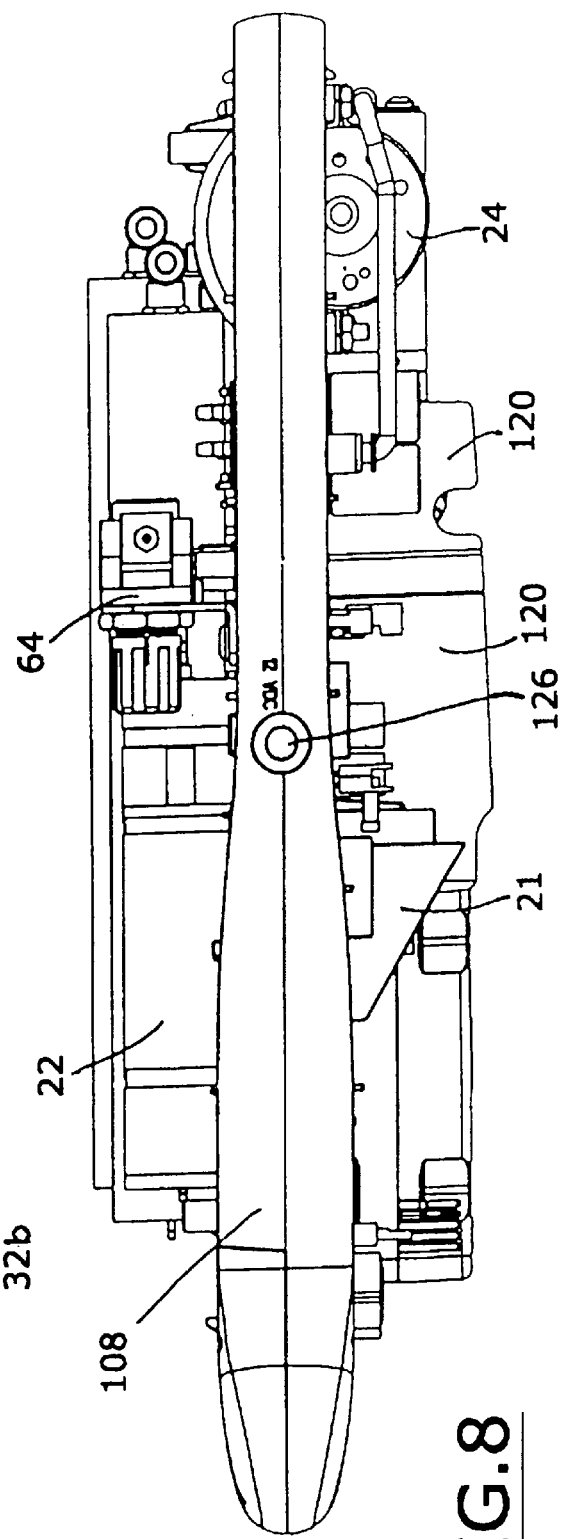
Figure 9:
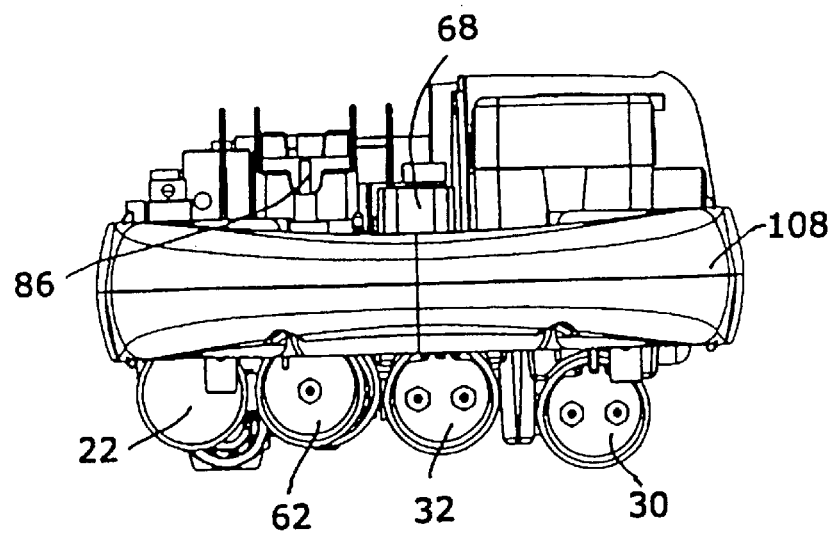

Control assembly 60, to which the usable portion of the produced gas directed according to the invention, includes a mixing tank 62 which also may be filled with synthetic zeolite and serves as a reservoir to store product oxygen before delivery to the user through an apparatus outlet 68 in the pulse dose mode, a piston-type pressure control regulator 64 to regulate the product gas pressure to be delivered to the user, a bacteria filter 66, and an oxygen delivery system 70 including a pulse dose transducer 72 including the OCD components of the electronic circuit 80 to be described, a flow control solenoid operated valve 74, and a low pressure sensor 76. As shown in FIGS. 2, 3 and 5, all of the feed, waste, equalization and flow control valves are mounted on a common valve block 26.

According to the invention, delivery of the PSA generated oxygen concentrated gas from the mixing tank 62 to the user is controlled by the delivery system 70 as will now be described.

As is well known, the most effective use of inhaled oxygen occurs at the onset of inhalation, and various devices have been constructed to deliver oxygen from pressurized oxygen tanks only when inhalation is first sensed by the devices and only during the initial stage of the inhalation cycle. We have taken advantage of that well known principle to devise a much more compact and efficient PSA apparatus to include an oxygen delivery system that primarily only delivers oxygen at the initial stage of inhalation. As shown in the drawing, for example in FIGS. 11 and 12, low pressure sensor 76 will detect a drop in pressure as sensed by inhalation of a user through a conventional cannula (not shown) connected to the apparatus outlet 68 by which the oxygen concentrated gas is delivered to the user. When pressure sensor 76 detects the pressure drop, the transducer circuitry 72 in electronic circuit 80 causes the flow control valve 74 to be opened for a predetermined time and allow a predetermined amount of the oxygen enriched gas in the mixing tank 62 to be delivered to the user through the outlet 68. The amount of delivered gas is controlled by the electronic circuit 80 on circuit board 81 and using a programmable device 77 for delivery of any one of a number of effective flow rates, which in our preferred embodiment include five effective flow rates of one through five LPM at an oxygen concentration from about 80% to about 95%.

The setting is made by the multiple position control switch 86 which, as shown in FIG. 2, is accessed by opening a hinged cover 102 on an upper housing portion 104 of the apparatus 20. Cover 102 preferably is held closed by a magnetic latch for both a secure closure and easy opening. Apparatus 20 is further enclosed by a lower housing portion 106. Between the upper and lower housing portions 104, 106 and mating with them is a central chassis 108 on which are mounted the operating components of the apparatus 20.

The outer housing portions 104, 106 and the chassis 108 may be of any suitable impact resistant material, but preferably is an injection molded ABS plastic. Chassis 108 as shown also includes an integrally molded carry handle 109.

The effectiveness and compact size of the invention is made possible in large part because of structural placement of the components of the invention and control of air flow within the apparatus as will now be described.

According to the invention, ambient air can enter the interior of the apparatus 20 only into the space between the access cover 102 and control panel 111, which is accomplished by access vents 110 in a recess surrounding outlet 68 and through an elongated slot 112 formed at the hinge connection of cover 102 to the upper housing 104. Except for the access vents 110, the slot 112, and at air exhaust points, the upper and lower housings 104 and 106 form an enclosed chamber with the chassis 108. The ambient air is caused by a fan 92 to enter the enclosed interior enclosed chamber of apparatus 20 through an accessible inlet filter 113 on control panel 111 which may be accessed when hinged cover 102 is opened. Filter 113 is a foam, gross-particulate filter designed to remove dust and other impurities, from the air entering the apparatus interior. A portion of the ambient air which enters the interior of apparatus 20 through filter 113 is caused by the compressor assembly 24 to flow into the intake 21 of the resonator 22 through a second filter 114 made of felt material to further filter the air to be fractionated. The balance of the ambient air flowing into the interior of the apparatus 20 is, according to the invention, caused to flow in a controlled path throughout the enclosed interior of the apparatus to cool the operating elements of the PSA assembly.

Figure 10:
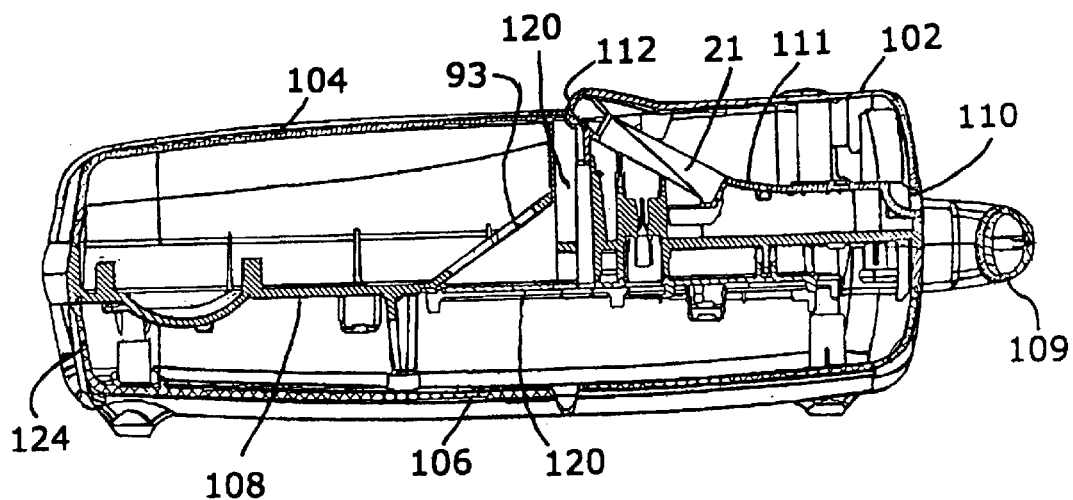
FIG. 10 is a cross sectional view taken on line 10—10 of FIG. 5.

As will become evident, fan 92, which is positioned in an angled opening 93 in chassis 108 as shown in FIG. 10, also functions to move the balance of the ambient air in a controlled path through the enclosed spaces in the apparatus 20 between the chassis 108 and the cover portions 104, 106.

As can be seen in FIGS. 4–9, the operating elements mounted on the top side of the central chassis 108 are the intake 21, control switch 86, accessible through control panel 111, to activate the apparatus and set the flow rate, a removable battery pack 90, the valve block 26, the compressor assembly 24, the circuit board 81, the fan 92, and the cannula fitting 68. Mounted on the bottom side of the central chassis are the resonator 22, the adsorber beds 30, 32, the muffler 46, the mixing tank 62, and the pressure control regulator 64.

To direct the flow throughout the apparatus 20 of the ambient air used for cooling the operating components of the apparatus 20, the portion of the ambient air entering at filtered inlet 113 and not directed through filter 114 is directed through the apparatus by a series of horizontal and vertical baffles 120 formed with chassis 108 and which direct the ambient cooling air entering the access space through filtered inlet 113, by the draw from fan 92, sequentially over the circuit board 81, the valve block 26 and compressor assembly 24. The ambient cooling air is then drawn by fan 92 to the underside of the chassis 108 through opening 93, first through a plenum or duct (not shown) formed on the bottom side of chassis 108, to direct all of the cooling air toward the front of the space formed between chassis 108 and lower housing 106. The cooling air is then redirected to flow toward the back of apparatus 20 over the resonator 22, adsorber beds 30, 32, mixing tank 62, muffler 46 and pressure regulator 64 before being expelled through grillwork 124 at the rear end of the lower housing portion 106. As will be evident from FIG. 12 to be described, all of the heat generating components mounted on circuit board 81, which is mounted on the top of chassis 108, are positioned on the rear side of the circuit board in the direct flow of the cooling air as it enters the interior of apparatus 20.

Because of the novel design and combination and placement of elements comprising the invention, a combined PSA/OCD based on the preferred embodiment is easily able to deliver an oxygen concentration, at standard atmosphere of about 90%±3% in pulse doses at every inhalation cycle of about 8.75 mL for the setting of 1 LPM, about 17.5 mL for the setting of 2 LPM, about 26.25 mL for the setting of 3 LPM, about 35.0 mL for the setting of 4 LPM, and about 43.75 mL for the setting of 5 LPM. Quite surprisingly, this performance can be achieved in an apparatus with a weight of less than about 10 lb., measuring less overall than 17" in length, 8" in width and 6" in height, and emitting less than about 55 decibels noise level.

In the embodiments shown, each of the adsorber beds 30, 32 for a medical application may be about 9.75 inches in length and about 1.25 inches in diameter, with the zeolite sieve material weighing about 81 grams for each adsorber bed. Preferably, the beds 30, 32 are spring biased in order not to "fluidize" the sieve material in their depressurization or pressure equalization stages. The feed stream of air is provided at a nominal rate of about 7 liters per minute, to produce a product gas within an approximate operating pressure range from about 19 psia to about 23 psia, or about 21 psia when powered at about 13 volts, with the setting at 3 LPM and a user breathing rate of about fifteen breaths per minute.

The circuit components on the printed circuit board 81 control the PSA cycle and the pulse dosing of oxygen from the apparatus. Those components are illustrated in FIGS. 11a–f and 12 and function as described in the attached detailed description of circuit 80.

The concentration of the oxygen supplied by the apparatus for each flow control switch setting is dependent on system pressure, operating voltage (battery or external supply), and patient breathing rate within allowable ranges of these parameters. In circuit 80 as will be shown, the microprocessor calculates, from continuous or sampled readings of the selector position, the operating voltage, and the frequency of actuation of the OCD, the predictable oxygen concentration being delivered to the user. If any of these approach the upper or lower thresholds, for example as low as 85% oxygen concentration, an intermittent alarm may be provided to warn the user that he or she can continue to use the apparatus but should take action to prevent the performance from falling outside of specifications. If any of the parameters regularly exceeds the predetermined thresholds, for example at a calculated oxygen concentration of 80% or less, the alarm may be programmed to sound continuously to notify the user that the performance of apparatus 20 is outside of specifications and its use discontinued.

Figure 13:
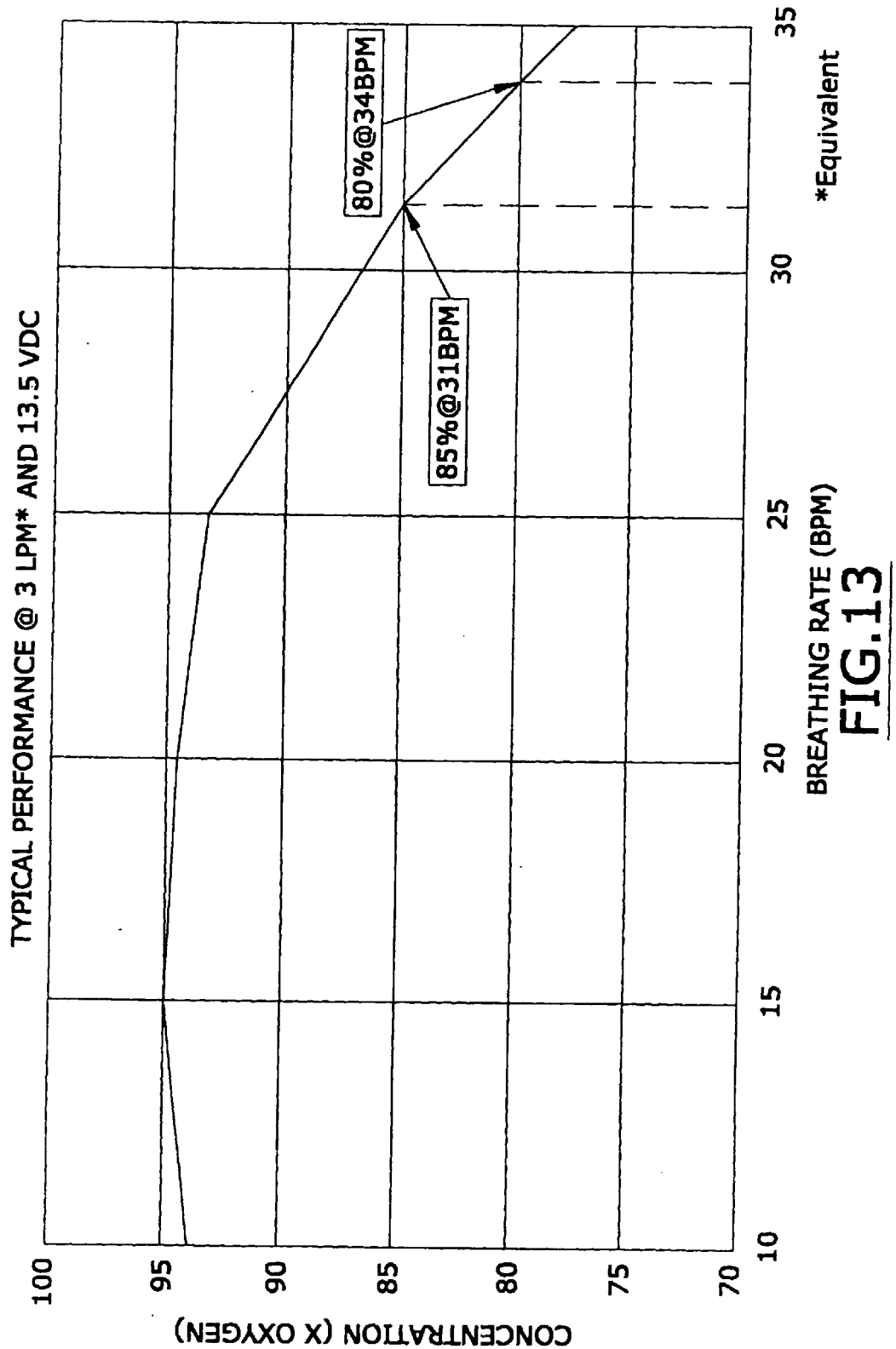
FIG. 13 is a graph approximating the effect that the breathing rate of a user may have on the relative concentration of oxygen as supplied by the preferred embodiment.

For example, although the apparatus has been designed to accommodate reasonable breathing rates, a very significant increase in the physical activity of a user and the resulting increased breathing rate could cause the apparatus to be overdrawn by a demand of oxygen from the apparatus 20 more than it can supply. The graph of FIG. 13 illustrates the effect breathing rate has on oxygen concentration for a flow control switch setting of 3 LPM and a supply voltage of 13.5 VDC.

The embodiment shown preferably includes an audible signal at startup of the apparatus, both audible and a red visual light alarms to signal high and low pressure, system overdraw, and an apnea event (i.e., the absence of inhalation within a preset time), audible and yellow visual light alarms to signal a low battery condition, and a pulsing green light to indicate normal apparatus operation in a pulse mode.

Maximum breathing rates for the apparatus have been determined for the combination of each flow control switch setting and range of voltages that control the apparatus. The circuit 80 continuously monitors the battery voltage, flow control switch setting, and the patient's breathing rate. If the breathing rate causes the apparatus to approach an overdraw condition (an oxygen concentration of about 85%) or to reach overdraw (a concentration of about 80% or less), the alarm either warns or alerts the patient to moderate his or her physical activity.

Mounted on the circuit board and below filter 113 is a conventional liquid crystal display hour meter 122 to record the cumulative time of use of the apparatus, so that the recommended service scheduling can be met. As filter 113 is removable by the user for washing, hour meter 122 can be easily seen by the user. During servicing, a test button 87 accessible from the control panel may be actuated to cause the apparatus 20 to cycle through its various operating modes to ensure that operating components of the apparatus function as designed. An accessible reset button 130 enables a service technician to reset the counter on the hour meter after servicing.

A temperature switch 124 is provided to shut off power to the compressor assembly 24 in the event of overheating as a result of, e.g., cooling fan failure or air inlet/outlet blockage.

Figure 11A:
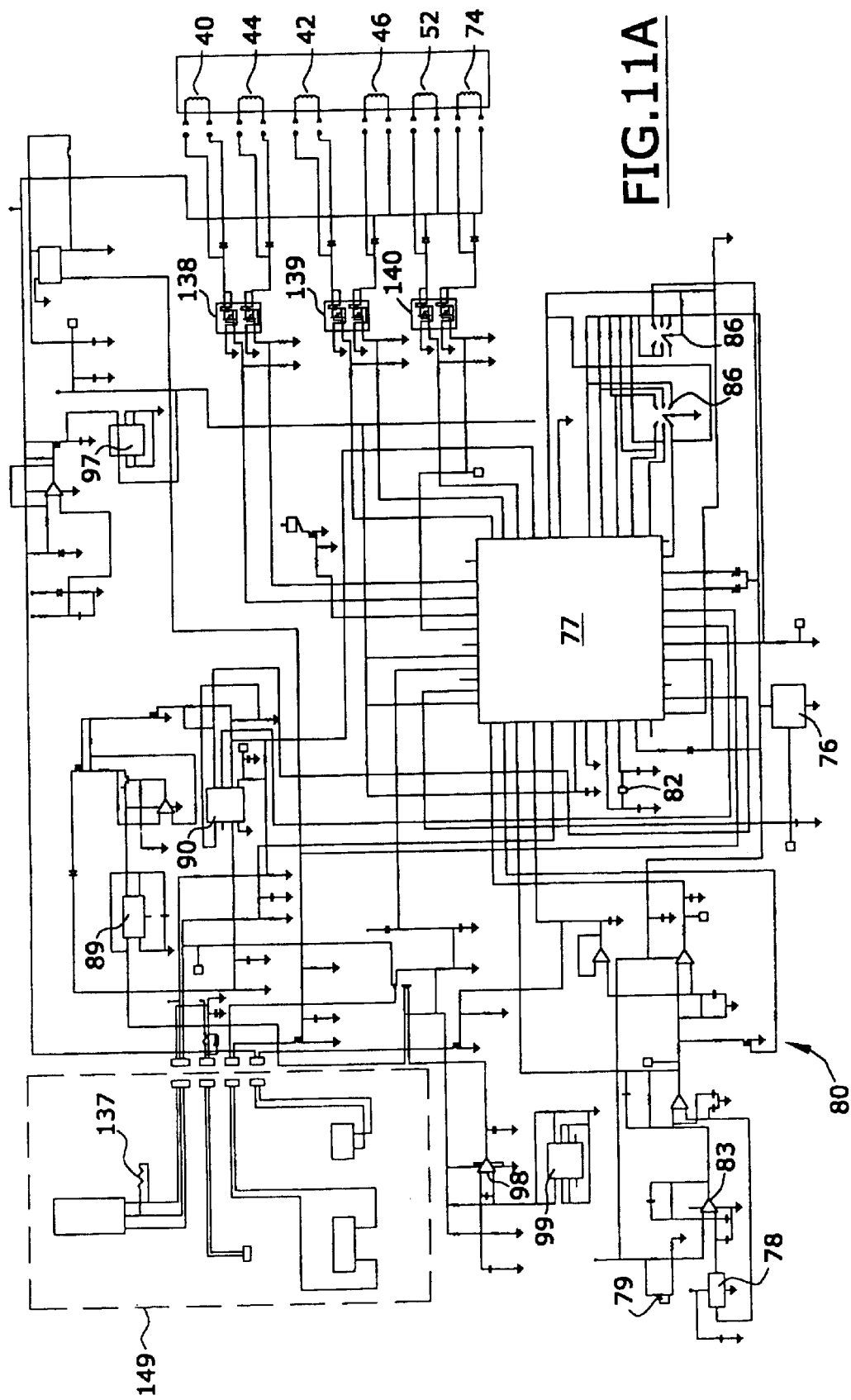
Figure 12:
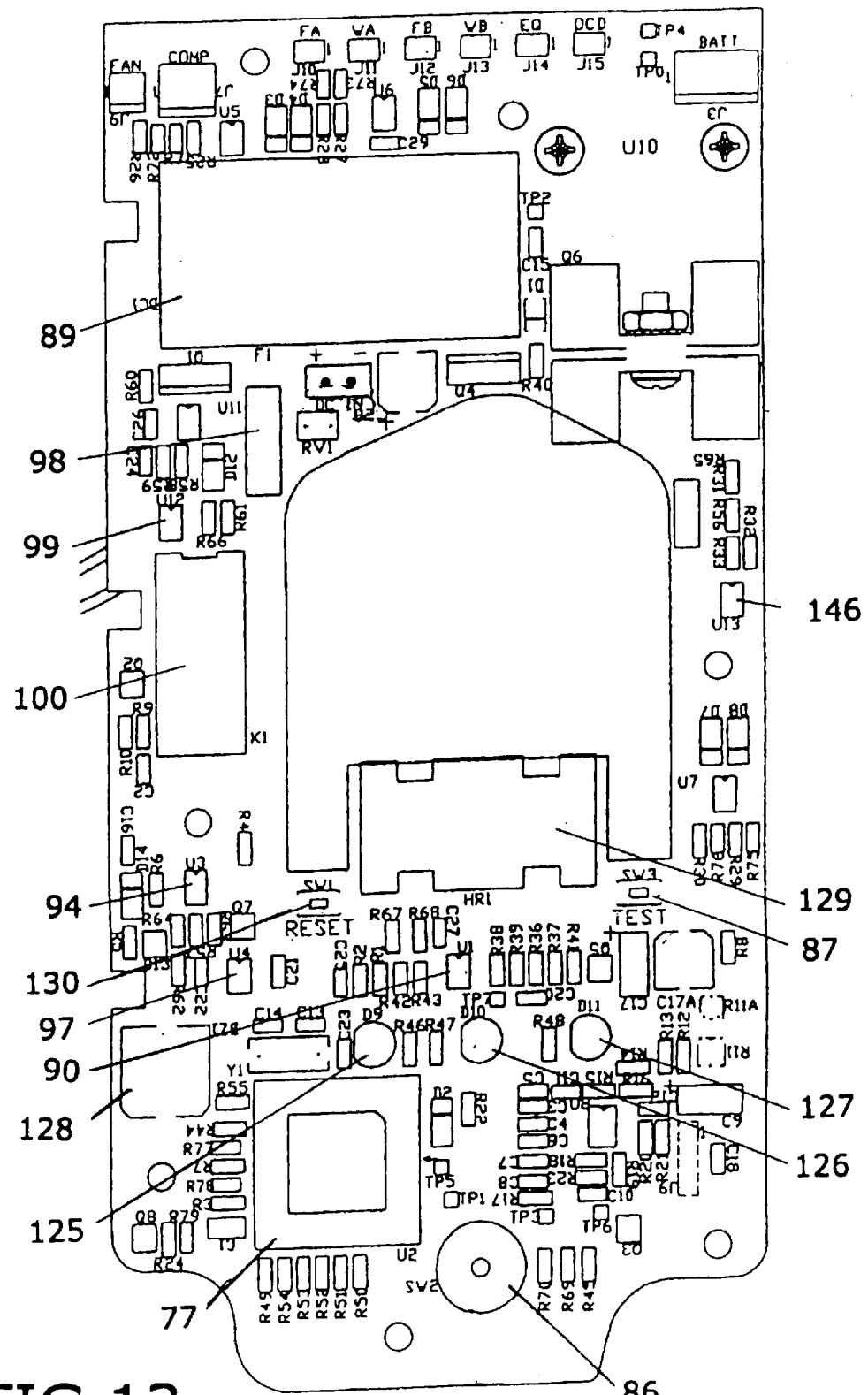
FIG. 12 illustrates the circuit board.

As shown in FIG. 11A, the main circuit board 81 is based on the PIC 16F74-1/L microcontroller 77, having an external crystal oscillator 82 with a clock rate of 1 Mhz. The microcontroller 77 receives input data from: 1.) the analog pressure conditioning circuit (for the oxygen conserving device, hereinafter OCD), 2.) the battery management system with a nominal 1.5 amp constant current generator, 3.)

the valve control 72 (for the pressure swing adsorption, hereinafter PSA), 4.) a rotary switch 86, 5.) the purity test button 87, and 6.) the pressure sensor 76 to indicate sensor pressure. The microcontroller 77 communicates with the operator via three LEDs 125,126 and 127, and an audible alarm 128. Additionally, an hour meter 122 will indicate compressor on time.

Referring to FIG. 11D and FIG. 11C, two additional circuits reside on the main circuit board 81. The battery reset circuit disables the 5V regulator 97 when the battery voltage drops below a reference voltage, effectively shutting down the majority of the circuit board and minimizing the current drawn from the battery. The second circuit controls the switching response time of the on-board circuit relay K1 100, providing uninterrupted service if the AC adapter is removed. The relay 100 is energized when the external power supply is plugged into the unit, so that the unit is energized from the external supply only. When the external supply is unplugged the relay 100 will de-energize, and the unit will operate on battery power.

FIG. 11B is a schematic diagram of the pressure signal conditioning circuit or OCD. A quadruple operational amplifier, OPA4336EA250, is used in the analog section of the circuitry. Two of the four amplifiers, U8-A 83 and U8-B 84, have inputs connected directly to the differential output of the pressure transducer U9 78. An optimum offset voltage on Pin 7 of U8-B 84 was determined to be 3.475±0.025 volts. This voltage is set by adjusting trimmer R11 79. The gain of this stage is over 400; as a result, the pressure signal on Pin 7 of U8-B 84 is in the right range for the following stage to make decisions regarding patient breathing. Amplifier U8-C 88 is configured as a comparator. Pin 12 of 88 represents the average pressure in the patient cannula during the last four-to-five breaths, while Pin 11 of 88 instantaneously follows the breathing pressure. As a result, a vacuum generated during the initial part of each inhalation changes the output of U8-C 88 from low to high, signaling a new inhalation to the microcontroller 77. One of the advantages of using this circuit is its relative immunity to small or slow offset drifts caused by temperature changes or component aging. In addition, the "floating" average pressure signal automatically follows changes in the breathing pattern.

When the solenoid valve 74 is open and oxygen flows through the cannula, a relatively high pressure is present in the system. This pressure is read by the pressure sensor U9 78 and amplified by U8-A 83 and U8-B 84, generating a five-volt spike in the output of U8-B 84. To maintain the accurate average pressure value, influenced only by patient breathing, this spike is compensated for by a counter-pulse generated by transistor Q3 85. The gate of this transistor is activated by a signal from the microcontroller U2 77 for as long as the signal on Pin 7 of U8-B 84 is higher than 4.375 volts. When Q3 85 is on, the resulting voltage on Pin 11 of U8-C 88 is very close to the voltage of no pressure being present in the cannula, thereby preventing the average pressure from being influenced by the pressure associated with the flow of oxygen.

The battery management system, as shown in FIG. 11C, consists of a benchmark BQ2002TSN (U1) battery management chip 91, a Burr-Brown operational amplifier, UPA2334UA (U13) 146, an Astec DC—DC 5 volt converter (DC-1) 89, an MJE3055T power transistor (Q6) 131, and two supporting MOSFET transistors, IRF9Z34 (Q4) 132 and BS170 (Q5) 133. The operation of this circuit follows: The microcontroller 77 controls the supply voltage (VDD) to the battery-management chip 91. The battery-management chip 91 reads battery voltage via resistors R1 134 and R2 135. When power is applied via the external power supply, the microcontroller Pin 36 supplies five volts to Pin 6 of the battery-management chip 91, turning it on. When power is first applied to the battery-management chip, it goes to a fast-charge charging cycle. The cycle causes Pin 8 of the battery-management chip 91 to output five volts and turn on Q5 133 which turns on Q4 132, allowing a nominal 1.5 amps of current to flow into the battery.

The nominal 1.5 amps of current is derived from the constant-current generator that consists of U13 99, a DC—DC 5 volt converter (DC-1) 89, power transistor (Q6) 131; and two supporting MOSFET transistors (Q4) 132 and (Q5) 133. The operation of this circuit follows: The DC—DC converter 89 raises the external 13.5 volt power-supply voltage to 18.5 volts. When a five-volt signal is present on Pin 8 of the battery-management chip 91, Q5 133 turns on and then turns on Q4 132. Now the Burr Brown op-amp U13 99 measures the differential voltage across R65 136. When the voltage across R65 136 is 75 mV, the Burr-Brown op-amp maintains Q6 131 so that 1.5 amps of current flows through it as long as Pin 8 of the battery-management chip 91 is at logic high (five volts).

The battery-management chip 91 monitors the charging cycle through Pin #5, the TS pin. This pin, in conjunction with a 10 k thermistor 137 in the battery pack, provides temperature feedback from the battery pack in the form of voltage. The TS pin samples the voltage from the battery every 19 seconds and compares it to the three samples measured earlier. If the voltage has fallen 25 mV or more, fast charge is terminated.

The valve control (PSA) is illustrated in FIG. 11D. The microcontroller controls valve drivers U5 138, U6 139 and U7 140. These consist of the PSA valves 40, 42, 44, 46, 52 and the OCD valve 74.

Each PSA valve is turned on via the drivers according to the following timing sequence:

| Open Valve | Open Time |
|---|---|
| FB, WA | 6 sec |
| FA, EQ | 1 sec |
| FA, WB | 6 sec |
| FB, EQ | 1 sec |

FA = Feed valve A (40)
FB = Feed valve B (42)
WA = Waste valve A (44)
WB = Waste valve B (46)
EQ = Equalizing valve (52)

The OCD valve 74 is turned on every time the pressure-signaling conditioning circuit detects a breath from the user. The time that the OCD valve 74 is on depends upon the setting of the flow-selector switch 86.

| Flow Selector Setting | On Time |
|---|---|
| 1 | 82 ms |
| 2 | 120 ms |
| 3 | 172 ms |
| 4 | 250 ms |
| 5 | 310 ms |

The rotary switch 86 is illustrated in FIG. 11E. The microcontroller 77 reads the condition of the rotary switch 86 to determine whether the unit is on or off and what flow selection the user has chosen. The unit is in the OFF position when the microcontroller 77 reads the logic low on Pin 28 of the microcontroller 77. A logic high on Pin 28 of the microcontroller 77 indicates that the unit has been turned ON. The microcontroller 77 reads the flow selection of the rotary switch 86 via Pins 29 through 33 of microcontroller 77. The flow selection is read for Position 1 when a logic low is read on Pin 29 of the microcontroller 77. Flow selection 2 is read when a logic low is read on Pin 30 of the microcontroller 77. This process repeats itself for Pins 31 through 33 for flow selections 3 through 5. The purity test button SW3 87, also illustrated in FIG. 11E, is a normally-open switch and is used to put the microcontroller 77 in one of two test modes. When the switch is in its normally-open position, a logic high is applied to Pin 18 of the microcontroller 77, indicating normal operation. When the switch is pressed, the microcontroller 77 reads a logic low on Pin 18 and reads the condition of the rotary switch SW2 86 to determine which of the two test modes it must run. If the rotary switch 86 is set to any flow selection between 1 and 4, the unit breathes 15 breaths per minute defaulting to flow selection 3. This is the first-test condition. The second test is initiated if the flow-selector switch is set to Position 5 and the purity test switch SW3 87 is pressed. In this test mode, the unit breaths the following breaths per minute for three-minute intervals: 15, 17.5, 20, 22.5, 25, 27.5, 30. Both test modes continue until the unit is switched off. When the unit is turned back on again, it resumes normal operation.

The rotary switch 86 is illustrated in FIG. F. The microcontroller 77 reads the condition of the rotary switch 86 to determine whether the unit is on or off and what flow selection the user has chosen. The unit is in the OFF position when the microcontroller 77 reads the logic low on Pin 28 of the microcontroller 77. A logic high on Pin 28 of the microcontroller 77 indicates that the unit has been turned ON. The microcontroller 77 reads the flow selection of the rotary switch via Pins 29 through 33 of microcontroller 77. The flow selection is read for Position 1 when a logic low is read on Pin 29 of the microcontroller 77. Flow selection 2 is read when a logic low is read on Pin 30 of the microcontroller 77. This process repeats itself for Pins 31 through 33 for flow selections 3 through 5. The purity test button SW3 87, also illustrated in FIG. F, is a normally-open switch and is used to put the microcontroller 77 in one of two test modes. When the switch is in its normally-open position, a logic high is applied to Pin 18 of the microcontroller (U2) 77, indicating normal operation. When the switch is pressed, the microcontroller 77 reads a logic low on Pin 18 and reads the condition of the rotary switch SW2 86 to determine which of the two test modes it must run. If the rotary switch SW1 is set to any flow selection between 1 and 4, the unit breathes 15 breaths per minute defaulting to flow selection 3. This is the first-test condition. The second test is initiated if the flow-selector switch is set to Position 5 and the purity test switch SW3 87 is pressed. In this test mode, the unit breaths the following breaths per minute for three-minute intervals: 15, 17.5, 20, 22.5, 25, 27.5, 30. Both test modes continue until the unit is switched off. When the unit is turned back on again, it resumes normal operation.

The pressure sensor 76 is illustrated in FIG. 11A. The high-pressure circuitry is based on Motorola pressure sensor MPX5500DP (U10) 76. The microcontroller 77 Pin 5 reads the analog output from the pressure sensor 76. When the pressure sensor is at two psi or lower, the microcontroller 77 signals a system failure. This condition repeats itself if the system pressure is 36 psi or higher. In addition, there is a pre-condition alarm that activates if the system pressure is 33 psi.

The Three LED's (one red, one green, one yellow) and a buzzer 128 are also illustrated in FIG. 11F and FIG. 11D. The green LED, D9 125, is used during a 1.2 second start-up sequence to tell the user that he or she is turning on the unit. Green LED 130 also will flash each time a breath is detected and a pulse dose is delivered to the user. The yellow LED, D10 126, is used for battery charging when the unit is in the OFF condition. When the yellow LED is flashing, the unit is charging the battery. When the yellow LED 126 comes to a constant, non-flashing state, the battery is fully charged. This process takes approximately two hours and is visible only when the unit is in the OFF position. When the unit is turned ON and running off the external battery (no external power supply), the microcontroller 77 reads the battery voltage via resistor divider network R67, R68, and Pin 11 of microcontroller 77. When the battery voltage decays to 10.9 volts, the yellow LED 126 and the buzzer 128 come on for one second for every five seconds they are off. This indicates to the user that the battery is in a low condition and should be charged or replaced to continue operation. When the battery decays to 10.5 volts, the unit automatically shuts down and flashes the yellow LED 126 and buzzer 128 on and off at a frequency of 500-milliseconds. The red LED 127 is used as a pre-condition alarm, a system failure alarm, or an apnea alarm. The table below lists the alarms and alarm functions.

TABLE of Alarms

| Audible Alarm | Visual Alarm | Indication | What to do |
| --- | --- | --- | --- |
| 5-second continuous audible alarm at startup | None | unit has been turned on. | You may begin to operate the |
| None | Battery-Yellow Flashing when unit is OFF and plugged into power source | Battery is charging. | If the unit is unplugged from the power source and used, the battery does not supply power for the full 50 minutes. |
| None | Battery-Yellow Non-Flashing when unit is OFF and plugged into power source | Battery is fully charged. | If the unit is unplugged from the power source and used, the battery supplies power for the full 50 minutes. |
| Continuous audible alarm | Alarm-RED Non-flashing | No breath has been sensed for 30 seconds. | Check the cannula connection. Ensure that |

-continued

TABLE of Alarms

| Audible Alarm | Visual Alarm | Indication | What to do |
| --- | --- | --- | --- |
| | | | you are breathing through your nose. If the alarm persists, contact your Equipment Provider. |
| 1-second beep every 5 seconds | Battery-YELLOW Flashing | Battery requires charging | Replace the battery, or plug the apparatus into an automobile cigarette lighter or a 120 volt outlet within 5 minutes. |
| ½-second beep every ½ second. | Battery-YELLOW Flashing | Battery voltage is too low to operate apparatus. | Replace the battery, or plug the apparatus into an automobile cigarette lighter or a 120 volt outlet immediately. |
| Three ½-second beeps followed by a 5 second pause | Alarm-RED Flashing | Breathing rate is approaching the threshold of the apparatus capacity; or the apparatus is approaching general malfunction. | Reduce activity, and/or locate another source of oxygen. The apparatus can be operated in this condition. |
| ½-second beep every ½ second | Alarm-RED Flashing | Breathing rate is exceeding the capacity of the apparatus. | Reduce activity, and/or locate and use another source of oxygen. Contact your Equipment Provider. |
| ½-second beep every ½ second | Alarm-RED Non-flashing | General malfunction of the apparatus has occurred. | Change to another source of oxgen, and contact equipment provider. Turn off the apparatus. |

The HR1 hour meter 122 as illustrated in FIG. 11D collects time when the compressor is running, up to 99,999 hours for 11 years. There is a reset button, SW1 130, that when pressed by a service technician, resets the hours to 0. The meter needs no external power source to maintain memory content.

The battery-reset circuit as shown by FIG. 11D consists of a micropower comparator, TLV3401IDR (U3) 94, a 1.2 volt reference, D13 95, two resistor divider networks R4, R6 and R5, R6, a P-Channel MOSFET transistor ZXM61P03CT (Q7) 96, and a five-volt regulator, LM78L05ACM (U4) 97. When an external power supply is plugged into the unit, the voltage divider network R5 and R6 is higher than the 1.2 volt reference, which keeps the output Pin 6 of the micropower comparator U3 94 1 low. This low output in turn keeps Q7 96 1 on, supplying voltage to the input of the five-volt regulator (U4) 97. With the external power supply plugged in, the circuit remains in this state, and the circuit board has a valid five volts from which to operate. When the battery is used with no external power supply, resistor divider network R4 and R6 monitor the battery voltage. When the battery decays to below ten volts, the voltage on Pin 2 of the micropower comparator (U3) 94 is lower than the 1.2 volt reference. This forces the output Pin 6 of the micropower comparator (U3) 94 high. This in turn turns off Q7 96, which shuts down the five-volt regulator U4 97. In this condition the circuit board draws approximately 175 uA current from the battery. The circuit remains in this condition until the battery voltage is raised above ten volts or until the external power supply is plugged in again.

The on-board relay circuit as shown in FIG. 11B consists of comparator U11 (LM311) 98 and voltage reference U12 (LM431) 99. This circuit speeds up the switching time of the relay when the external power supply is unplugged from the unit and the battery must take over. During design and testing, it was found that, when the external supply is removed from the unit, a back emf from the compressor motor holds the relay open long enough for the microcontroller 77 to reset before the battery voltage can take over and run the circuit. When the compressor is removed, the switching time for the relay is adequate to switch the external power supply voltage to the battery voltage without resetting the microcontroller 77. The circuit functions as follows: when the external power supply is first plugged into the unit, the voltage at resistor divider network R58 and R59 is above the three-volt reference set by U12 (LM431) 99. This condition forces the output of U11 (LM311) 98 to be high, thereby turning on the relay K1 100 as shown in FIG. 11C. When the external power supply is removed from the unit, the voltage across the relay coil begins to decay. When the voltage across the relay coil K1 100 reaches eight volts, resistor dividers R58 and R59 divide this voltage so that it is below the three-volt reference set by U12 (LM431) 99. This forces the output of U11 (LM311) 98 low, closing the relay (K1) 100 regardless of what is happening with the compressor. This prevents microcontroller resets during external and battery power-supply exchanges.

Figure 14:
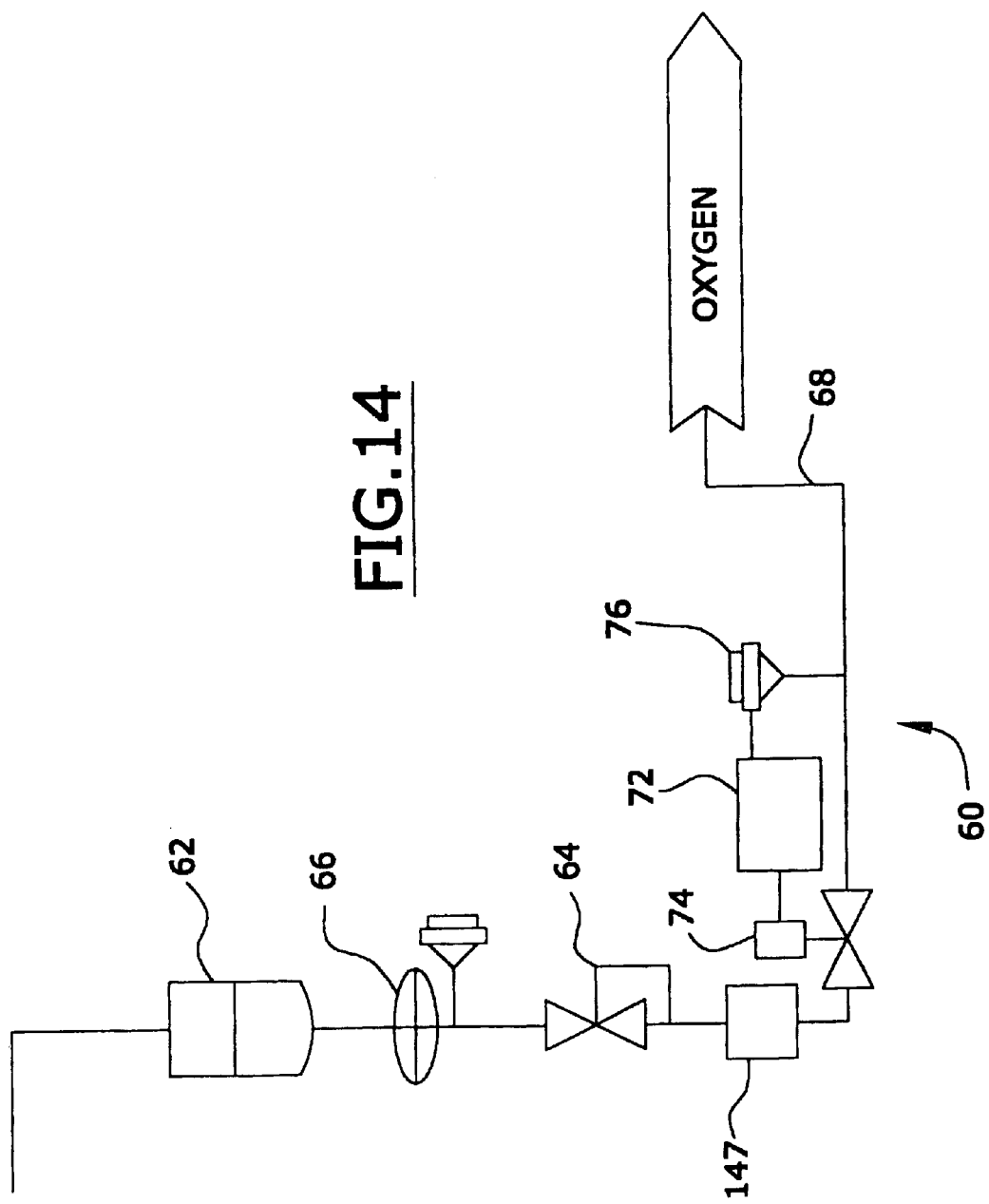
FIGS. 14 and 14A partially illustrate an alternate embodiment in which the apparatus also includes an oxygen monitor.
Figure 14A:
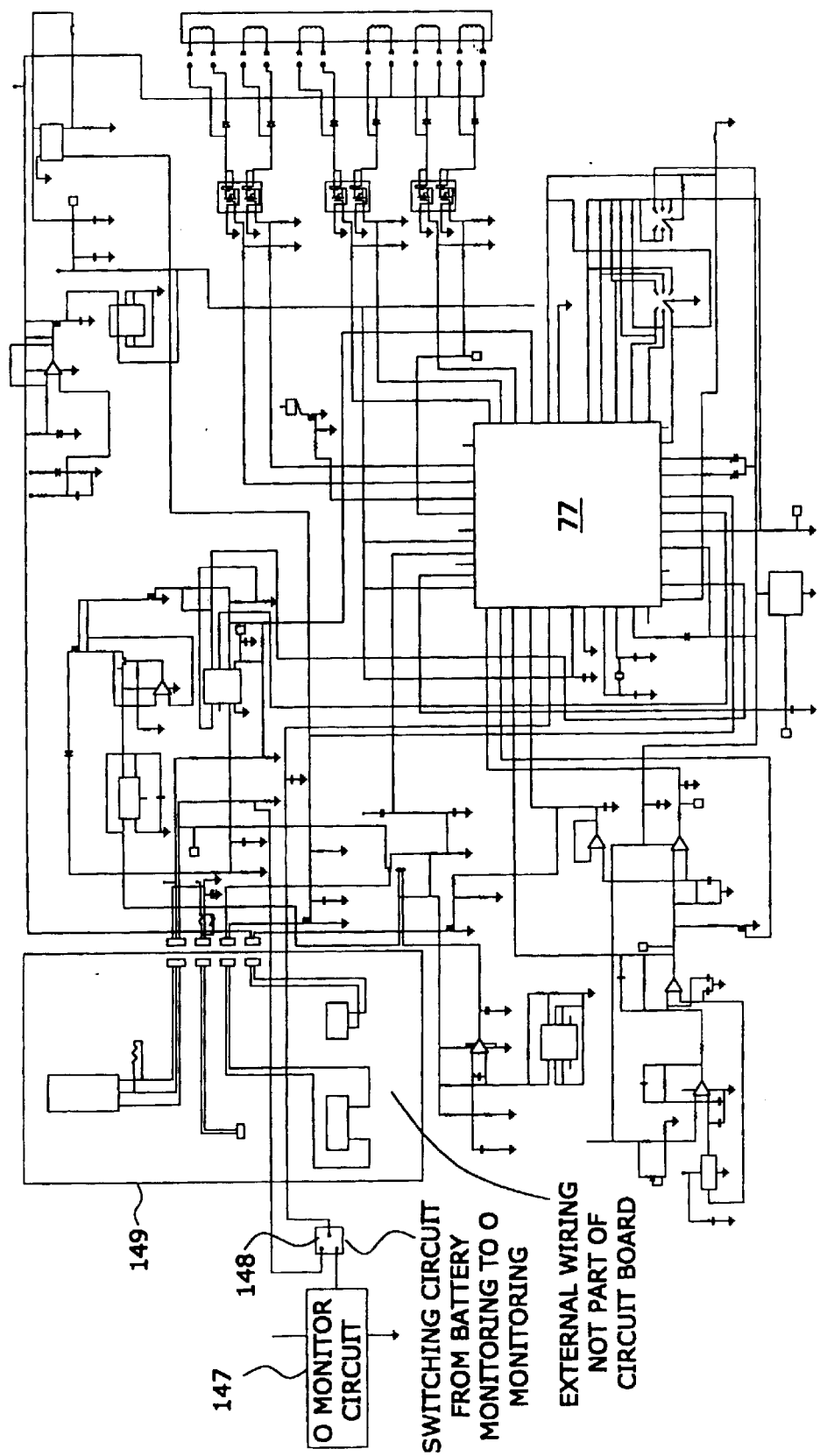

In the embodiment described above, the microprocessor monitors battery voltage, system pressure and flow rate. Additional embodiments are planned to include an Oxygen monitoring system. One possible position for the oxygen monitoring system 147 is illustrated in FIG. 14. This particular embodiment depicts the oxygen monitoring system 147 in-line before the oxygen delivery system. The oxygen monitoring system 147 is positioned between the pressure control regulator 64 and the flow control valve, however other possible positions are possible. The output of the oxygen sensor 147 will be monitored by the microprocessor 77, as shown in FIG. 14a. In this particular embodiment, the oxygen monitoring system 147 will share microprocessor 77 pin 11 with the battery monitoring system 149. A switching circuit 148 for switching between the oxygen monitoring system 147 and the battery monitoring system 149 is shown in FIG. 14a

Although the apparatus according to our invention is shown by a preferred embodiment, those skilled in the art will be able, from the description of our invention as herein provided, to produce a combined PSA/OCD apparatus, the individual fluid, electric and electronic components and controls of which can be found in the art or made by one skilled in the art following a reading of this description of the preferred embodiment. It also is possible to use a three bed PSA as described in co-pending U.S. application Ser. No. 09/851,750, pending filed May 9, 2001, pending the use of which may not require a mixing tank because of the relatively constant output pressure achieved by a PSA made according to that invention. It also is possible, as illustrated schematically in FIGS. 14 and 14B, to include a known oxygen monitor to measure the actual rather than the calculated concentration of oxygen being delivered to the user. In addition, those skilled in the art may be able to include other known safety features for use in monitored and/or unmonitored medical purposes. If it also is desired to be able to variably control the concentration of oxygen in the product gas, then it also may be possible to incorporate into the invention a second adjustable purge loop, not shown but described in U.S. Pat. No. 5,871,564.

To operate the apparatus 20 the user accessible rotary switch 86 is turned to the desired "equivalent" flow rate on the operating panel both to turn on the PSA operation and to deliver oxygen at the set rate. At start-up of the apparatus, all of valves of valve block 26 are open to eliminate any back pressure and then either left open or closed in sequence through a timing mechanism of conventional switches and relay switches in programmable circuit 80. As each of the feed, waste, and equalization valves is preferably a solenoid-type valve responsive to a turning on or shutting off of power to the valve, product-producing and regeneration operations are automatically controlled in apparatus 20 by automatically controlling the amount of time that each of the feed, waste, and equalization valves are opened and closed.

As shown and described, the apparatus can be powered any one of three sources, including a removable, nickel metal hydride battery pack which when fully charged can supply power to the apparatus for approximately 50 minutes without external power; an AC adapter to connect the apparatus at connector 126 to a nominal 120 volt AC outlet to convert the 120 volt AC to 13.5 volt DC; and a "cigarette lighter" adapter for a similar connection to a nominal 13.5 volt DC automobile battery. As shown, both the AC adapter and the automobile battery can power the apparatus and recharge the battery pack simultaneously, taking approximately two hours to charge the battery pack. Similarly, the battery pack may be detached from the apparatus by conventional plug means to facilitate the use of fully-charged spare battery packs.

It will be understood that various modifications and substitutions may be made to the described embodiment without departing from the spirit of the invention. Accordingly, the described preferred embodiment is intended for purposes of illustration and not as a limitation.

What is claimed is:

1. A compact and portable oxygen delivery apparatus for medical uses by producing from ambient air a product gas having a high concentration of oxygen and delivering the product gas to a user of the apparatus, the apparatus comprising a chassis having two opposing sides, a pressure swing adsorption unit mounted on the chassis and comprising at least one adsorber bed mounted on one of the sides to receive ambient air and adsorb nitrogen from the ambient air to produce the oxygen concentrated product gas, a product delivery unit for receiving at least a substantial portion of the product gas from the pressure swing adsorption unit, control means for delivering the product gas to the user at selectable rates during inhalation by the user, means for receiving the ambient air, valve means mounted on one of the sides for controlling the flow of both the ambient air and the product gas, and means for directing additional ambient air to cool the adsorber bed, the receiving means and the valve means by controlling the pattern of flow of the additional ambient air, in which the directing means comprises first and second housing portions mounted, respectively, on the opposing sides of the chassis and forming an interior space between each of the housing portions and its respective chassis side, the receiving means comprising a fan to draw air into one of the spaces, and baffle means positioned between the chassis and at least one of the housing portions for controlling the direction of flow of the additional ambient air.

2. The apparatus according to claim 1, in which the ambient air receiving means further comprises a compressor to supply the ambient air under pressure to the adsorber bed, and the product delivery unit comprises a storage tank to receive product gas from the adsorber bed and a pressure regulator to control the pressure of the product gas to be delivered to the user, the compressor mounted on the other chassis side with the valve means, and the storage tank and the pressure regulator mounted on the one chassis with the adsorber bed.

3. The apparatus according to claim 2, in which the ambient air receiving means further comprises a resonator to reduce the noise level of the intake air, the pressure swing adsorption unit further comprising means including a noise muffler for expelling the adsorbed nitrogen from the apparatus, the resonator and the muffler mounted on the one chassis side.

4. The apparatus according to claim 3, in which the additional ambient air is caused to flow in sequence over the valve means, the compressor, through the fan and then over the adsorber bed, storage tank, resonator and muffler.

5. The apparatus according to claim 4, in which the first housing portion defines access means for enabling ambient air to be drawn into the apparatus, and the second housing portion defines means enabling the additional ambient air to be expelled from the apparatus.

6. The apparatus according to claim 1, and further comprising means mounted on the chassis for setting and/or monitoring the effective flow rate and/or concentration of the product gas, and in which one of the housing portions comprises a movable section to enable access to the setting means.

7. The apparatus according to claim 6, and further comprising means on the chassis for receiving an electrical power source.

8. The apparatus according to claim 1, and further comprising a carry handle formed with the chassis.

9. The apparatus according to claim 1, in which the control means comprises means for sensing inhalation by the user, and programmed means for delivering product gas to the user at a regulated pressure for predetermined selectable times during inhalation, and the valve means including a product delivery valve to be opened only during the selected times.

10. The apparatus according to claim 9 and further comprising at least one alarm to alert the user if the oxygen concentration in the product gas being delivered is below a predetermined amount.

11. The pressure swing adsorption apparatus of claim 9 in which the oxygen concentrated product gas is produced to be delivered at effective rates from about one liter per minute to about five liters per minute and with a concentration of about 90% oxygen.

12. The apparatus according to claim 1, and further comprising an oxygen monitor to measure the concentration of oxygen in the product gas.

13. The apparatus according to claim 12, and further comprising alarm means responsive to the oxygen monitor to warn the user when the concentration is outside a predetermined range.

14. The apparatus according to claim 1, in which the control means comprises a power source, means for measuring voltage input from the power source, means for selecting the flow rates for delivering the product gas to the user and responsive to inhalation by the user for activating the flow of product gas, and means responsive to the voltage, selecting means and the rate of activation for signaling a warning and/or an alarm when the concentration of the product gas is outside a predetermined range.

15. The apparatus according to claim 1, in which the ambient air receiving means comprises a compressor to pressurize a portion of the ambient air from which the product gas is produced, and wherein the control means, the compressor and the valve means are mounted on one side of the chassis in the interior space between the first housing portion and the one chassis side, the adsorber bed and the delivery means are mounted on the other side of the chassis in the interior space between the second housing portion and the other chassis side.

16. The apparatus according to claim 15, wherein fan and baffle means are positioned to draw ambient air into the interior space between the first housing portion and the one chassis side, and the balance of the ambient air not used to produce product gas first is drawn over the control means, the compressor and the valve means and then is redirected to the interior space between the second housing portion and the other chassis side to be drawn over the adsorber bed and the delivery means before being expelled from the apparatus.

* * * * *